(12) United States Patent
Cully et al.

(10) Patent No.: US 8,313,503 B2
(45) Date of Patent: Nov. 20, 2012

(54) ENDOLUMINAL DEVICES

(75) Inventors: Edward H. Cully, Flagstaff, AZ (US);
K. Jason Nackard, Flagstaff, AZ (US);
Michael J. Vonesh, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 10/907,975

(22) Filed: Apr. 22, 2005

(65) Prior Publication Data

US 2005/0177186 A1 Aug. 11, 2005

Related U.S. Application Data

(62) Division of application No. 10/113,724, filed on Apr. 1, 2002, now abandoned.

(51) Int. Cl.
*A61M 29/00* (2006.01)
(52) U.S. Cl. .................................................. 606/200
(58) Field of Classification Search ............... 623/1.16, 623/1.11, 1.12, 1.23, 1.36; 606/200, 108, 606/194, 110, 113, 114, 159, 198
See application file for complete search history.

(56) References Cited

U.S. PATENT DOCUMENTS

| | | |
|---|---|---|
| 4,374,026 A | 2/1983 | Greutert |
| 4,425,908 A | 1/1984 | Simon |
| 4,723,549 A | 2/1988 | Wholey et al. |
| 5,133,733 A | 7/1992 | Rasmussen et al. |
| 5,192,286 A | 3/1993 | Phan et al. |
| 5,634,942 A | 6/1997 | Chevillon et al. .................. 623/1 |
| 5,695,518 A | 12/1997 | Laerum ........................... 606/200 |
| 5,695,519 A | 12/1997 | Summers et al. .............. 606/200 |
| 5,709,704 A | 1/1998 | Nott et al. |
| 5,735,892 A | 4/1998 | Myers et al. |
| 5,769,816 A | 6/1998 | Barbut et al. |
| 5,814,064 A | 9/1998 | Daniel et al. ................... 606/200 |
| 5,827,324 A | 10/1998 | Cassell et al. .................. 606/200 |
| 5,853,420 A | 12/1998 | Chevillon et al. .............. 606/200 |
| 5,876,367 A | 3/1999 | Kaganov et al. .................... 604/8 |
| 5,893,869 A | 4/1999 | Barnhart et al. ............... 606/200 |
| 5,902,475 A | 5/1999 | Trozera et al. ................. 205/655 |
| 5,907,893 A | 6/1999 | Zadno-Azizi et al. ........... 29/6.1 |

(Continued)

FOREIGN PATENT DOCUMENTS

EP 0812155 12/2003

(Continued)

OTHER PUBLICATIONS

Bamford J, et al. Incidence of Stroke in Oxfordshire: First Year's Experience of a Community Stroke Register. British Medical Journal 1983; 287:713-717.

(Continued)

*Primary Examiner* — Elizabeth Houston
(74) *Attorney, Agent, or Firm* — Fish & Richardson P.C.

(57) ABSTRACT

A seamless, self-expanding implantable device having a low profile is disclosed along with methods of making and using the same. The implantable device includes a frame cut out of a single piece of material that is formed into a three-dimensional shape. The implantable device may comprise an embolic filter, stent, or other implantable structure. The present invention also allows complicated frame structures to be easily formed from planar sheets of starting material, such as through laser cutting, stamping, photo-etching, or other cutting techniques.

19 Claims, 33 Drawing Sheets

U.S. PATENT DOCUMENTS

| | | | |
|---|---|---|---|
| 5,910,154 A | 6/1999 | Tsugita et al. | 606/200 |
| 5,911,734 A | 6/1999 | Tsugita et al. | 606/200 |
| 5,941,869 A | 8/1999 | Patterson et al. | 604/508 |
| 5,941,896 A | 8/1999 | Kerr | 606/200 |
| 5,980,552 A * | 11/1999 | Pinchasik et al. | 623/1.16 |
| 5,980,555 A | 11/1999 | Barbut et al. | |
| 5,989,281 A | 11/1999 | Barbut et al. | |
| 6,001,118 A | 12/1999 | Daniel et al. | 606/200 |
| 6,027,520 A | 2/2000 | Tsugita et al. | 606/200 |
| 6,042,598 A | 3/2000 | Tsugita et al. | 606/200 |
| 6,051,014 A | 4/2000 | Jang | 606/200 |
| 6,051,015 A | 4/2000 | Maahs | 606/200 |
| 6,053,932 A | 4/2000 | Daniel et al. | 606/200 |
| 6,058,914 A | 5/2000 | Suzuki | 123/538 |
| 6,059,814 A * | 5/2000 | Ladd | 606/200 |
| 6,066,149 A | 5/2000 | Samson et al. | 606/159 |
| 6,068,645 A | 5/2000 | Tu | 606/200 |
| 6,074,357 A | 6/2000 | Kaganov et al. | 604/8 |
| 6,083,215 A | 7/2000 | Milavetz | 604/509 |
| 6,090,097 A | 7/2000 | Barbut et al. | |
| 6,099,549 A | 8/2000 | Bosma et al. | 606/200 |
| 6,117,154 A | 9/2000 | Barbut et al. | |
| 6,129,739 A | 10/2000 | Khosravi | 606/200 |
| 6,136,016 A | 10/2000 | Barbut et al. | |
| 6,142,987 A | 11/2000 | Tsugita | 604/500 |
| 6,146,370 A | 11/2000 | Barbut | 604/504 |
| 6,152,946 A | 11/2000 | Broome et al. | 606/200 |
| 6,152,947 A | 11/2000 | Ambrisco et al. | 606/200 |
| 6,168,603 B1 | 1/2001 | Leslie et al. | |
| 6,168,604 B1 | 1/2001 | Cano | 606/114 |
| 6,168,622 B1 | 1/2001 | Mazzocchi | 623/1.2 |
| 6,171,327 B1 * | 1/2001 | Daniel et al. | 606/200 |
| 6,171,328 B1 | 1/2001 | Addis | 606/200 |
| 6,171,329 B1 | 1/2001 | Shaw et al. | |
| 6,179,859 B1 | 1/2001 | Bates et al. | |
| 6,187,025 B1 | 2/2001 | Machek | 606/200 |
| 6,224,612 B1 | 5/2001 | Bates et al. | |
| 6,231,544 B1 | 5/2001 | Tsugita et al. | |
| 6,231,589 B1 | 5/2001 | Wessman et al. | 606/200 |
| 6,235,045 B1 | 5/2001 | Barbut et al. | |
| 6,277,139 B1 | 8/2001 | Levinson et al. | |
| 6,327,772 B1 | 12/2001 | Zadno-Azizi et al. | 29/557 |
| 6,346,117 B1 | 2/2002 | Greenhalgh | |
| 6,361,546 B1 | 3/2002 | Khosravi | |
| 6,364,895 B1 | 4/2002 | Greenhalgh | |
| 6,371,969 B1 | 4/2002 | Tsugita et al. | |
| 6,371,970 B1 | 4/2002 | Khosravi et al. | |
| 6,375,670 B1 | 4/2002 | Greenhalgh | |
| 6,391,037 B1 | 5/2002 | Greenhalgh | |
| 6,391,044 B1 | 5/2002 | Yadav et al. | |
| 6,432,122 B1 | 8/2002 | Gilson et al. | |
| 6,485,501 B1 | 11/2002 | Green | |
| 6,511,496 B1 | 1/2003 | Huter et al. | |
| 6,511,497 B1 | 1/2003 | Braun et al. | |
| 6,517,559 B1 | 2/2003 | O'Connell | |
| 6,544,279 B1 | 4/2003 | Hopkins et al. | |
| 6,558,405 B1 * | 5/2003 | McInnes | 606/200 |
| 6,575,996 B1 * | 6/2003 | Denison et al. | 606/200 |
| 6,599,307 B1 | 7/2003 | Huter et al. | |
| 6,610,077 B1 * | 8/2003 | Hancock et al. | 606/200 |
| 6,730,117 B1 | 5/2004 | Tseng et al. | |
| 6,939,361 B1 * | 9/2005 | Kleshinski | 606/200 |
| 6,939,362 B2 * | 9/2005 | Boyle et al. | 606/200 |
| 7,241,304 B2 | 7/2007 | Boyle et al. | |
| 7,306,618 B2 | 12/2007 | Demond et al. | |
| 7,338,510 B2 | 3/2008 | Boylan et al. | |
| 2001/0044634 A1 | 11/2001 | Don Michael et al. | |
| 2001/0044652 A1 | 11/2001 | Moore | |
| 2002/0038767 A1 | 4/2002 | Trozera | 205/667 |
| 2002/0088531 A1 | 7/2002 | Cook et al. | |
| 2003/0065354 A1 * | 4/2003 | Boyle et al. | 606/200 |
| 2003/0065355 A1 * | 4/2003 | Weber | 606/200 |
| 2003/0139764 A1 | 7/2003 | Levinson et al. | |
| 2003/0144688 A1 | 7/2003 | Brady et al. | |
| 2003/0187474 A1 | 10/2003 | Keegan et al. | |

FOREIGN PATENT DOCUMENTS

| | | |
|---|---|---|
| EP | 1566148 | 8/2005 |
| GB | 2337002 | 11/1999 |
| WO | WO 98/33443 | 8/1998 |
| WO | 99/23976 | 5/1999 |
| WO | 99/44542 | 9/1999 |
| WO | 00/07521 | 2/2000 |
| WO | 00/16705 | 3/2000 |
| WO | 00/49970 | 8/2000 |
| WO | 00/67665 | 11/2000 |
| WO | 01/08595 | 2/2001 |
| WO | 01/19231 | 3/2001 |
| WO | 01/19260 | 3/2001 |
| WO | 01/45569 | 6/2001 |
| WO | 01/49215 | 7/2001 |
| WO | 03/011188 | 2/2003 |
| WO | 03/017823 | 3/2003 |
| WO | 03/035130 | 5/2003 |
| WO | 03/055412 | 7/2003 |
| WO | 03/063732 | 8/2003 |
| WO | 03/077799 | 9/2003 |

OTHER PUBLICATIONS

Barnett et al. Beneficial Effect of Carotid Endarterectomy. NE Journal of Medicine 1991; 325(7):446-453.

Hankey GJ. Investigation and Imaging Strategies in Acute Stroke and Transient Ischaemic Attacks. Hospital Update 1992; 107-124.

Robins M, et al. The National Survey of Stroke: The National Institute of Neurological and Communicative Disorders and Stroke. Office of Biometry and Field Studies Report. Chapter 4. Incidence. Stroke 1981; Part II; 12 (2):I-45 to I-57.

Theron JG et al. Carotid Artery Stenosis: Treatment With Protected Balloon Angioplasty and Stent Placement. Radiology 1996; 201:627-636.

Theron J, et al. New Triple Coaxial Catheter System for Carotid Angioplasty with Cerebral Protection. Amer J of Neuroradiology 1990; 11:869-874.

Yadav JS, et al. Elective Stenting of the Extracranial Carotid Arteries. Circulation 1997; 95:376-381.

Executive Committee for the Asymptomatic Carotid Atherosclerosis Study. Endarterectomy for Asymptomatic Carotid Artery Stenosis. JAMA 1995; 273(18): 1421-1461.

International Search Report and Written Opinion for PCT/US03/32962 (WO 04/034884).

Gunther RW and Vorwerk D. Minibasket for Percutaneous Embolectomy and Filter Protection Against Distal Embolization: Technical Note. Cardiovasc Intervent Radiol 1991; 14:195-98.

European Search Report, EP09007542, Jul. 28, 2009, Munich, 4 pages.

* cited by examiner

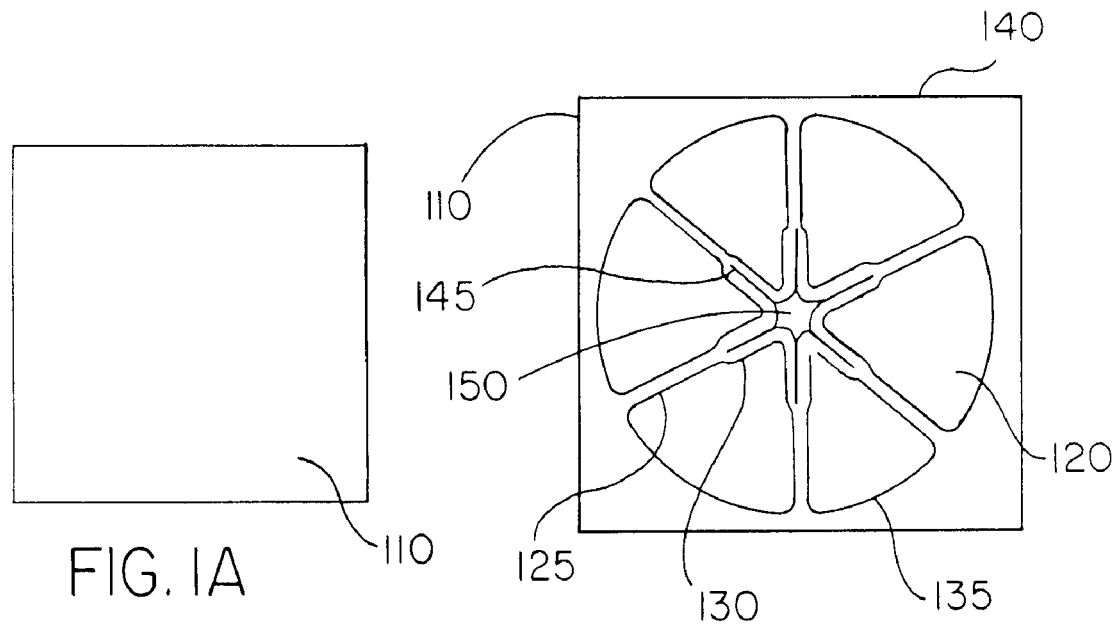
FIG. 1A
FIG. 1B
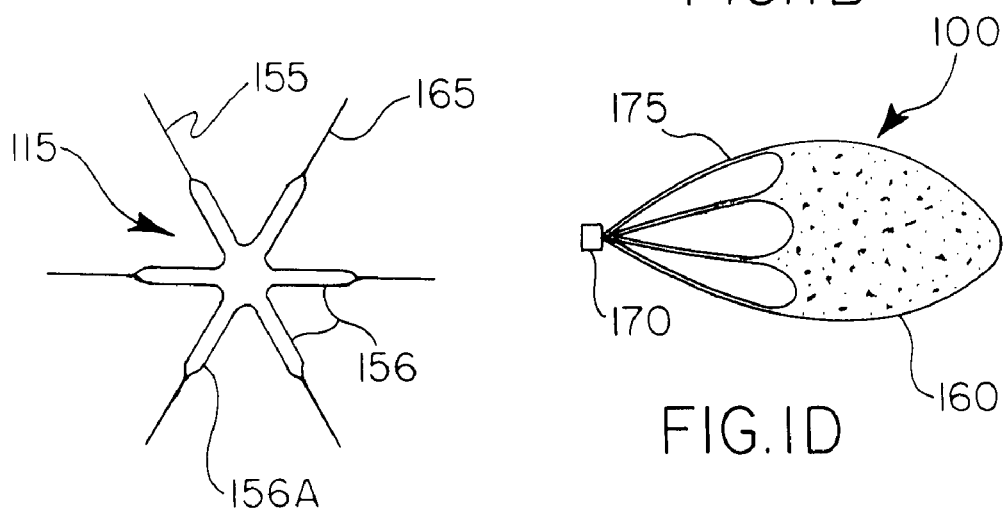
FIG. 1C
FIG. 1D
FIG. 1E

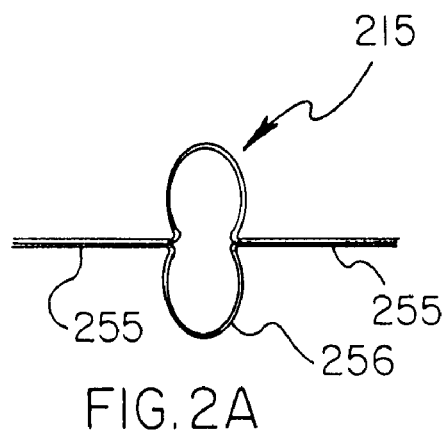
FIG. 2A
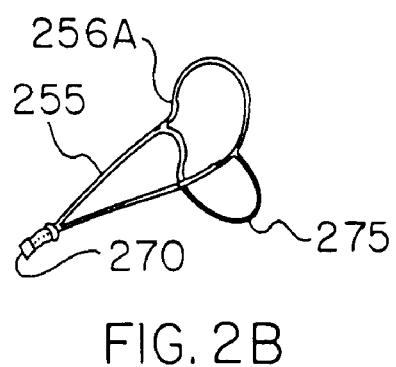
FIG. 2B
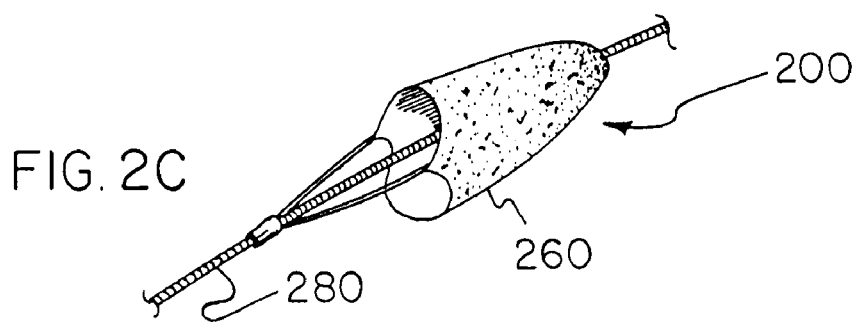
FIG. 2C
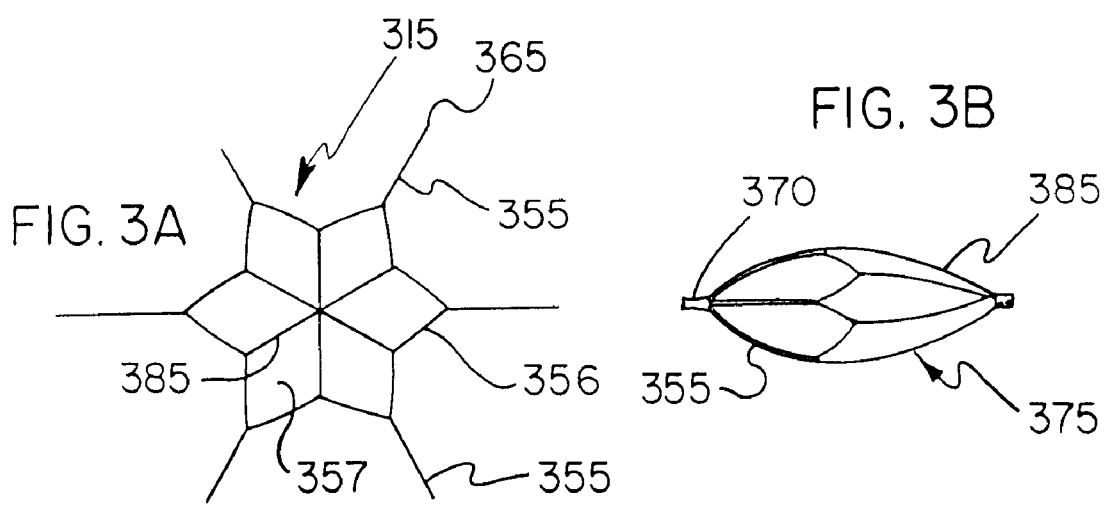
FIG. 3A
FIG. 3B
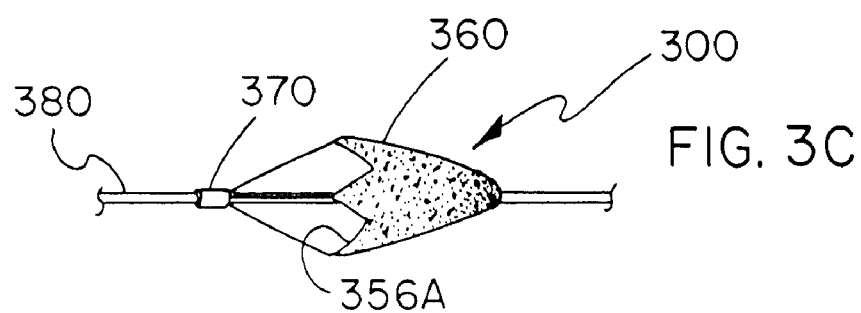
FIG. 3C

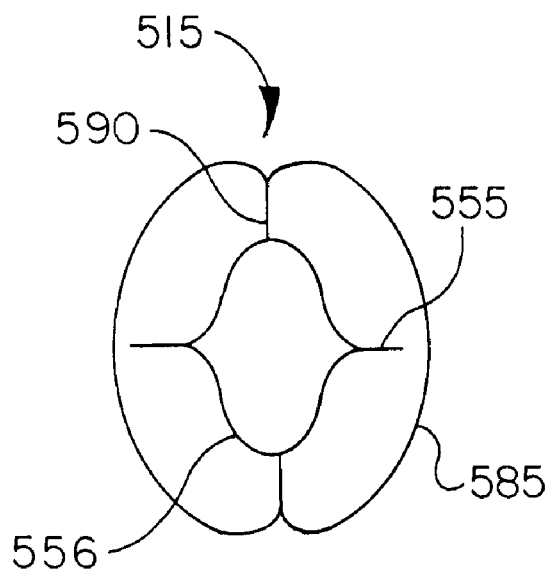
FIG. 5A
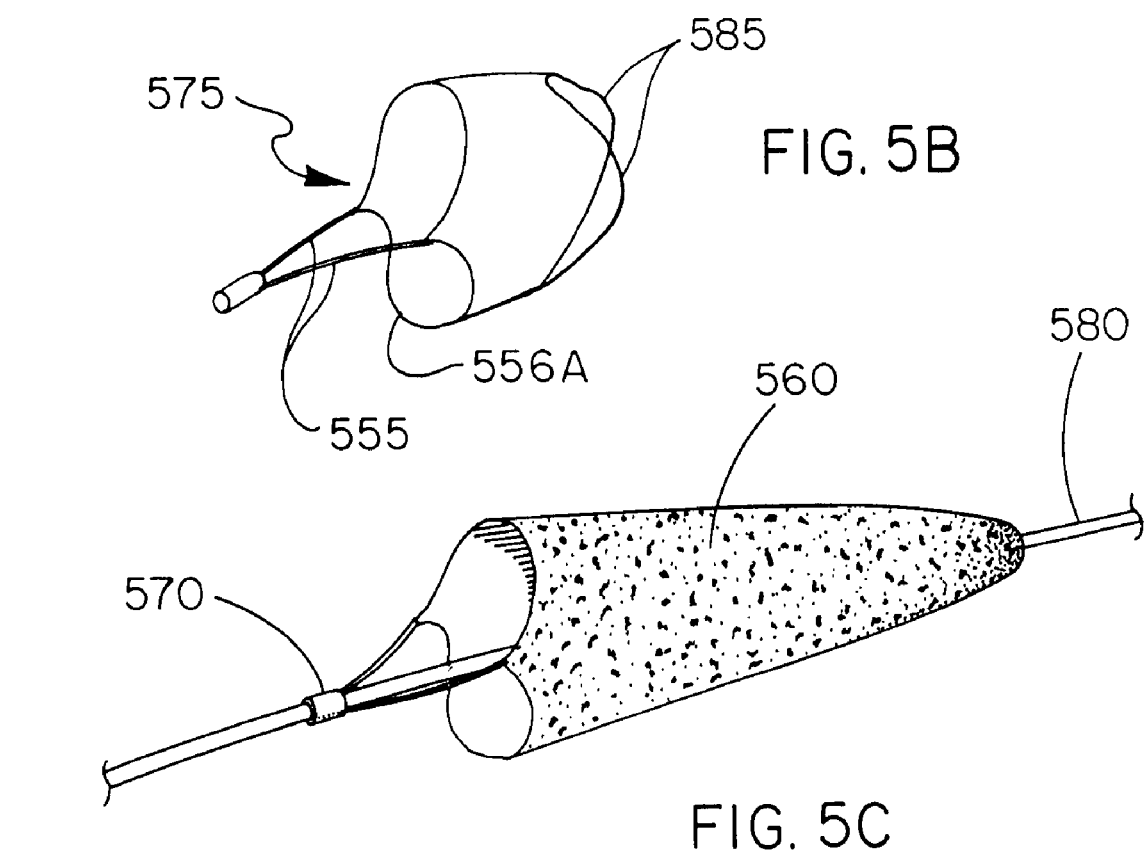
FIG. 5B
FIG. 5C

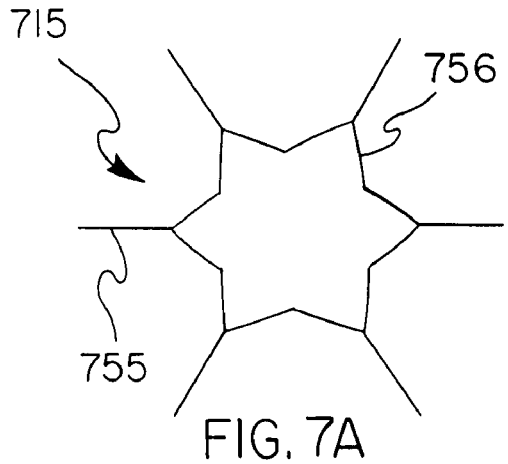
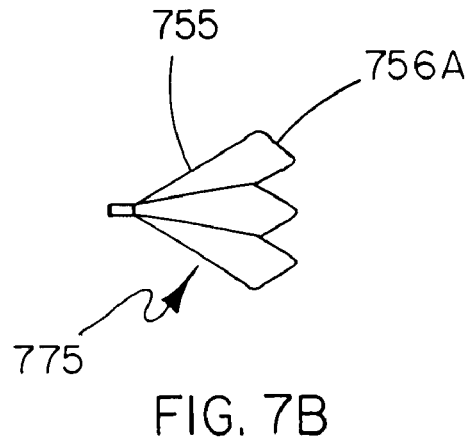
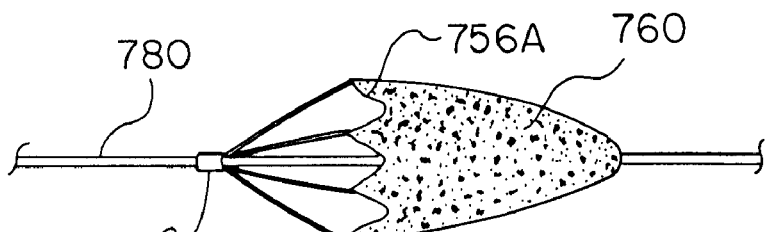
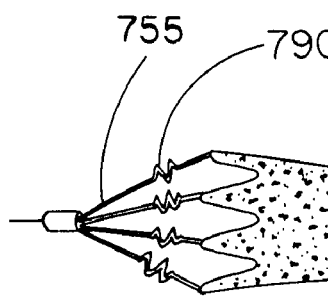
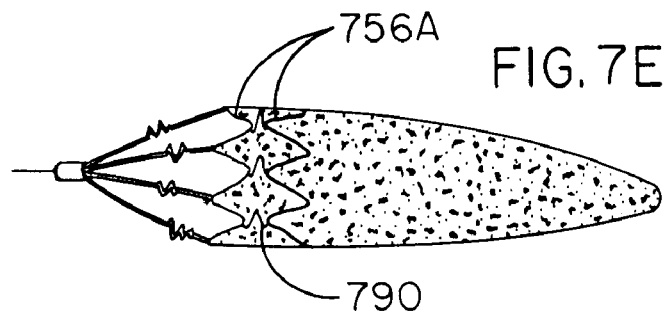

FIG.12A
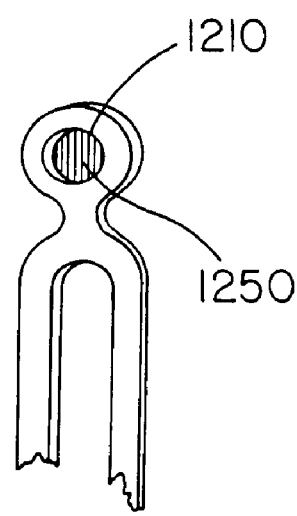
FIG.12B
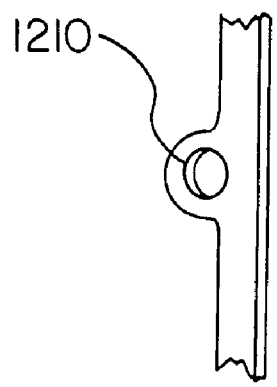
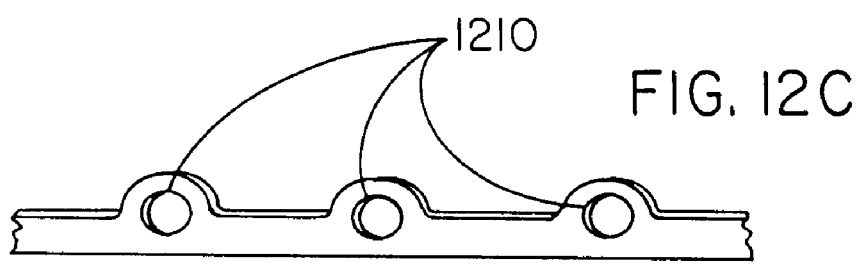
FIG.12C
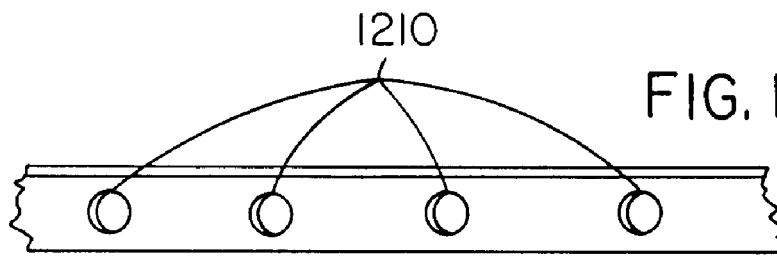
FIG.12D
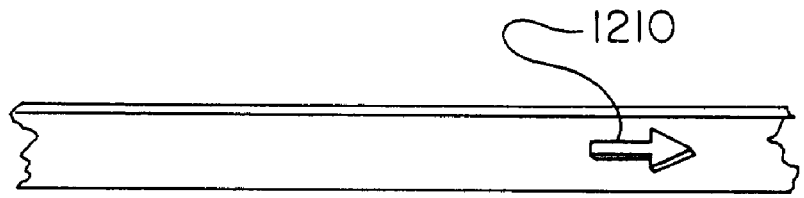
FIG.12E

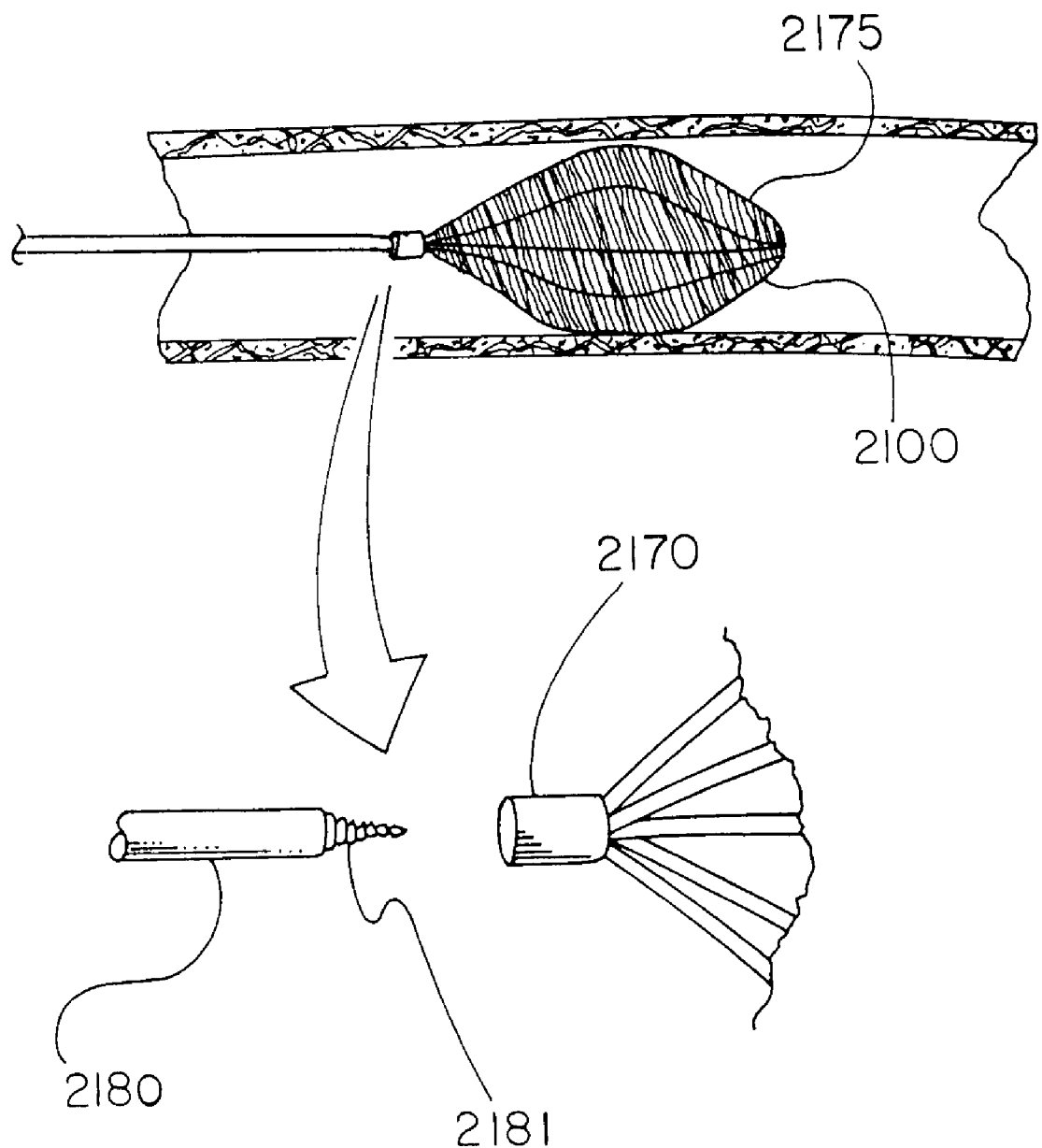

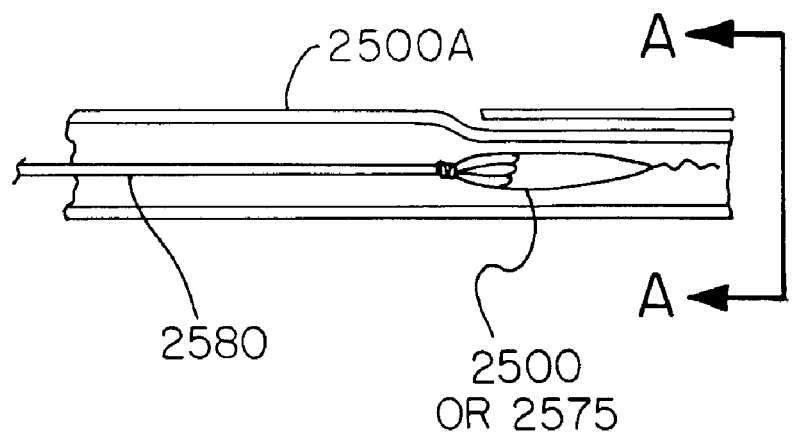
FIG. 25A
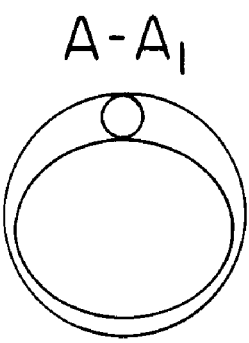 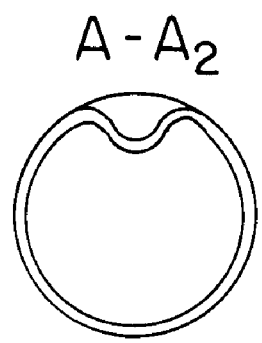 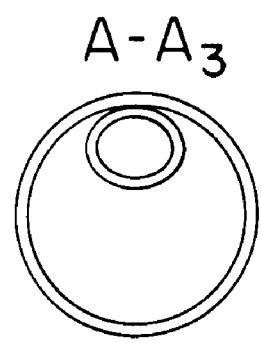
FIG. 25B    FIG. 25C    FIG. 25D $A_2-A_2$

ENDOLUMINAL DEVICES

CROSS-REFERENCE TO RELATED APPLICATIONS

This application is a Division of U.S. patent application Ser. No. 10/113,724 filed Apr. 1, 2002.

FIELD OF THE INVENTION

The present invention relates to seamless endoluminal devices including frame patterns for filters, their manufacture and use in the filtration and/or removal of embolic matter from fluids flowing in tubular body lumens including, but not limited to: blood flow in arteries and veins; airflow within the respiratory tract; and the flow of urine in the urinary tract. The seamless filter of the present invention may be self-expanding, is deployable via a guidewire-based system and has a low profile.

BACKGROUND OF THE INVENTION

Embolic protection is a concept of growing clinical importance directed at reducing the risk of embolic complications associated with interventional (i.e., transcatheter) and surgical procedures. In therapeutic vascular procedures, liberation of embolic debris (e.g., thrombus, clot, atheromatous plaque, etc.) can obstruct perfusion of the downstream vasculature, resulting in cellular ischemia and/or death. The therapeutic vascular procedures most commonly associated with adverse embolic complications include: carotid angioplasty with or without adjunctive stent placement and revascularization of degenerated saphenous vein grafts. Additionally, percutaneous transluminal coronary angioplasty (PTCA) with or without adjunctive stent placement, surgical coronary artery by-pass grafting, percutaneous renal artery revascularization, and endovascular aortic aneurysm repair have also been associated with complications attributable to atheromatous embolization. Intra-operative capture and removal of embolic debris, consequently, may improve patient outcomes by reducing the incidence of embolic complications.

The treatment of stenoses of the carotid bifurcation provides a good example of the emerging role of adjuvant embolic protection. Cerebrovascular stroke is a principle source of disability among adults, and is typically associated with stenoses of the carotid bifurcation. The current incidence of cerebrovascular stroke in Europe and the United States is about 200 per 100,000 population per annum (Bamford, *Oxfordshire community stroke project Incidence of stroke in Oxfordshire. First year's experience of a community stroke register. BMJ* 287: 713-717, 1983; Robins, *The national survey of stroke: the National Institute of Neurological and Communicative Disorders and Stroke. Office of Biometry and Field Studies Report. Chapter 4. Incidence. Stroke* 12 (Suppl. 1): 1-57, 1981). Approximately half of the patients suffering ischemic stroke have carotid artery stenoses (Hankey, *Investigation and imaging strategies in acute stroke and TIAs. Hospital Update* 107-124, 1992). Controlled studies have shown that the surgical procedure carotid endarterectomy (CEA) can reduce the incidence of stroke in patients compared to medical therapy with minimal perioperative complications (<6% for symptomatic patients with stenoses >70% [NASCET, *Beneficial effect of carotid endarterectomy in symptomatic patients with high grade stenoses. NEJM* 325: 445-453, 1991] and <3% for asymptomatic patients with 60% stenoses [ACAS, *Endarterectomy for asymptomatic carotid artery stenosis. JAMA* 273: 1321-1461, 1995]). These results provide convincing evidence of the benefit of treating carotid stenoses. Surgery, however, does have several limitations, including: increased mortality in patients with significant coronary disease (18%), restriction to the cervical portion of the extra-cranial vasculature, a predeliction for cranial palsies (7.6%-27%), and restenosis (5%-19%; Yadav, *Elective stenting of the extracranial carotid arteries. Circulation* 95: 376-381, 1997).

Carotid angioplasty and stenting have been advocated as potential alternatives to CEA. Percutaneous techniques have the potential to be less traumatic, less expensive, viable in the non-cervical extracranial vasculature, and amenable to patients whom might otherwise be inoperable (Yadav, *Elective stenting of the extracranial carotid arteries. Circulation* 95: 376-381, 1997). Despite the potential benefits of this approach, emboli liberated during trans-catheter carotid intervention can place the patient at risk of stroke. Emboli can be generated during initial accessing of the lesion, balloon pre-dilatation of the stenosis, and/or during stent deployment. Additionally, prolapse of atheromatous material through the interstices of the stent can embolize after the completion of the procedure.

The fear of dislodging an embolus from an atherosclerotic plaque has tempered the application of angioplasty and endovascular stenting to the supraaortic arteries and, particularly, to the carotid bifurcation (Theron, *New triple coaxial catheter system for carotid angioplasty with cerebral protection. AJNR* 11: 869-874, 1990). This concern is warranted due to the significant morbidity and/or mortality that such an event might produce. While the incidence of stroke may be at an acceptable level for the highly skilled practitioner, it is likely to increase as the procedure is performed by less experienced clinicians.

Embolic protection devices typically act as an intervening barrier between the source of the clot or plaque and the downstream vasculature. In order to address the issue of distal embolization, numerous apparatus have been developed and numerous methods of embolic protection have been used adjunctively with percutaneous interventional procedures. These techniques, although varied, have a number of desirable features including: intraluminal delivery, flexibility, trackability, small delivery profile to allow crossing of stenotic lesions, dimensional compatibility with conventional interventional implements, ability to minimize flow perturbations, thromboresistance, conformability of the barrier to the entire luminal cross-section (even if irregular), and a means of safely removing the embolic filter and trapped particulates.

For example, occlusion balloon techniques have been taught by the prior art and involve devices in which blood flow to the vasculature distal to the lesion is blocked by the inflation of an occlusive balloon positioned downstream to the site of intervention. Following therapy, the intraluminal compartment between the lesion site and the occlusion balloon is aspirated to evacuate any thrombus or atheromatous debris that may have been liberated during the interventional procedure. These techniques are described in Theron, *New triple coaxial catheter system for carotid angioplasty with cerebral protection. AJNR* 11: 869-874, 1990, and Theron, *Carotid artery stenosis: Treatment with protected balloon angioplasty and stent placement Radiology* 201:627-636, 1996, and are commercially embodied in the PercuSurge Guardwire Plus™ Temporary Occlusion and Aspiration System (Medtronic AVE). The principle drawback of occlusion balloon techniques stem from the fact that during actuation distal blood flow is completely inhibited, which can result in ischemic pain, distal stasis/thrombosis, and difficulties with fluoroscopic visualization due to contrast wash-out through the treated vascular segment.

Another prior system combines a therapeutic catheter (e.g., angioplasty balloon) and integral distal embolic filter. By incorporating a porous filter or embolus barrier at the distal end of a catheter, such as an angioplasty balloon catheter, particulates dislodged during an interventional procedure can be trapped and removed by the same therapeutic device responsible for the embolization. One known device includes a collapsible filter device positioned distal to a dilating balloon on the end of the balloon catheter. The filter comprises a plurality of resilient ribs secured to the circumference of the catheter that extend axially toward the dilating balloon. Filter material is secured to and between the ribs. The filter deploys as a filter balloon is inflated to form a cup-shaped trap. The filter, however, does not necessarily seal around the interior vessel wall. Thus, particles can pass between the filter and the vessel wall. The device also presents a large profile during positioning and is difficult to construct.

The prior art has also provided systems that combine a guidewire and an embolic filter. The filters are incorporated directly into the distal end of a guidewire system for intravascular blood filtration. Given the current trends in both surgical and interventional practice, these devices are potentially the most versatile in their potential applications.

These systems are typified by a filter frame that is attached to a guidewire that mechanically supports a porous filter element. The filter frame may include radially oriented struts, one or more circular hoops, or a pre-shaped basket configuration that deploys in the vessel. The filter element typically includes a polymeric mesh net, which is attached in whole or in part to the filter frame and/or guidewire. In operation, blood flowing through the vessel is forced through the mesh filter element thereby capturing embolic material in the filter.

Early devices of this type include a removable intravascular filter mounted on a hollow guidewire for entrapping and retaining emboli. The filter is deployable by manipulation of an actuating wire that extends from the filter into and through the hollow tube and out the proximal end. During positioning within a vessel, the filter material is not fully constrained so that, as the device is positioned through and past a clot, the filter material can potentially snag clot material creating freely floating emboli, prior to deployment.

In another prior art system an emboli capture device is mounted on the distal end of a guidewire. The filter material is coupled to a distal portion of the guidewire and is expanded across the lumen of a vessel by a fluid activated expandable member in communication with a lumen running the length of the guidewire. During positioning, as the device is passed through and beyond the clot, filter material may interact with the clot to produce emboli. This device may also be difficult to manufacture.

Another prior art device is adapted for deployment in a body vessel for collecting floating debris and emboli in a filter that includes a collapsible proximally tapered frame for operably supporting the filter between a collapsed insertion profile and an expanded deployment profile. The tapered collapsible frame includes a mouth that is sized to extend to the walls of the body vessel in the expanded deployed profile to seal the filter relative to the body vessel for collecting debris floating in the body vessel.

A further example of an embolic filter system involves a filter material fixed to cables or spines of a central guidewire. A movable core or fibers inside the guidewire can be utilized to transition the cables or spines from approximately parallel to the guidewire to approximately perpendicular to the guidewire. The filter, however, may not seal around the interior vessel wall. Thus, particles can pass between the filter and the entire vessel wall. This umbrella-type device is shallow when deployed so that, as it is being closed for removal, particles have the potential to escape.

Other disadvantages associated with the predicate devices are that the steerability of the guidewire may be altered as compared to the conventional guidewires due to the presence and size of the filter. The guidewire, for example, may bend, kink, and/or loop around in the vessel, making insertion of the filter through a complex vascular lesion difficult. Also, delivery of such devices in a low-profile pre-deployment configuration can be difficult. Further, some devices include complex and cumbersome actuation mechanisms. Also, retrieving such capture devices after they have captured emboli may be difficult. Further, when deployed in curved segments, the interaction of the guidewire and/or tether elements can deform the filter frame in such a way as to limit apposition to the host vessel wall, thereby allowing potential channels for passage of embolic debris. Also, the filter media of the prior art maintains a pore diameter of approximately 80 to 120 microns. It is desirable to minimize the pore size without adversely perturbing blood flow or being prone to clogging.

Current filter designs suffer from numerous disadvantages due to their construction. A typical wire filter is formed by manipulating multiple wires together through welding or some other form of attachment. After the wire frame is constructed, it is formed into the desired shape and a filter element is affixed onto the wire cage. A typical wire frame constructed in this manner is subject to a limited range of manipulation after the wires are adhered, since the welds or attachment areas are at an increased risk of failure due to the physical constraints of the welds themselves. A wire pair is more inclined to fracture at the weakest point, typically, a wire frame, composed of numerous wire pairs, will separate at the weld before separating in the length of the wire. Additionally, the welding of metal involves the application of increased heat to join a wire pair and a risk exists of the mesh, formed by the pairs, dripping or otherwise malforming due to the proclivity of metal to run before cooling.

A further disadvantage to a typical wire filter is that the filter element is difficult to apply to the frame since the filter is normally applied as a sock, tube, or other such shape. The typical wire frame is formed by welding and bending into the desired shape. The filter is then affixed onto the shaped wire frame by pulling the formed filter over the shaped wire frame. An additional problem evident in this construction is that the filter element could be abraded by a protrusion formed by a weld in a wire pair. Such an abrasion could form a weakness or a tear in the filter and undermine its desired functionality.

Simple and safe blood filtering and guidewire systems that can be temporarily placed in the vasculature to prevent distal embolization during endovascular procedures, and that can be used to introduce and/or exchange various instruments to a region of interest without compromising the position of the filter or guidewire, are required. Existing guidewire-based embolic filtering devices are inadequate for these and other purposes. The present apparatus, in contrast, provides a novel means of providing these and other functions, and has the further benefit of being easier to manufacture than the devices of the prior art.

SUMMARY OF THE INVENTION

The present invention relates to seamless implantable devices, filters, methods of manufacture, systems for deployment and methods of use.

One aspect of the present invention is to provide a low profile filter formed from a single piece of material.

Another aspect of the present invention is to provide a self-expanding filter that is seamless.

A further aspect of the present invention is to provide an integral self-expanding filter frame that is seamless.

A still further object of the present invention is to provide a seamless, low-profile filter that minimally perturbs flow.

A further aspect of the present invention to provide a low profile, seamless filter that is readily connected to the guidewire of a endoluminal deployment system.

A further aspect of the invention is to provide a filter apparatus, which maintains vessel wall apposition and a maximally open mouth when deployed in tortuous anatomy.

A further aspect of the invention is to provide a filter frame, which can be rendered sufficiently radiopaque.

A further aspect of the present invention is to provide filters which have increased capture efficiency and are capable of providing drug delivery.

A further aspect according to the present invention includes providing a seamless frame having a proximal end, a longitudinal axis, a seamless support member circumscribing the axis and distally spaced from the proximal end, and at least one attachment strut, and optionally at least one filter strut seamlessly extending from the support member.

Another aspect of the present invention is to provide a seamless frame having a proximal end, a longitudinal axis, a seamless support member circumscribing the axis and distally spaced from the proximal end, and at least one attachment strut, optionally at least one filter strut seamlessly extending from the support member, and at least one or more filter media layers.

Another aspect of the present invention is to provide implantable devices that may be configured as detachable devices designed for permanent implantation and/or subsequent retrieval and are used for: temporary vascular occluders; exclusion of bleeding varices or aneurysmal vascular segments; a stent, or similar means of providing structural support to an endoluminal cavity; a thrombectomy/atherectomy instrument; an implantable prosthetic vascular conduit wherein the proximal filter frame functions as an anchoring stent, and the distal filter is configured into an open-ended, tubular configuration (similar to a windsock) allowing endoluminal lining of a vascular segment with a biocompatible liner.

An aspect of the present invention is to provide seamless implantable devices formed from a single piece of material.

Another aspect of the present invention is to provide seamless implantable devices that have regions of articulation and/or radiopaque markers.

A further aspect of the present invention to provide seamless implantable devices that include radiopaque markers.

A still further aspect of the present invention is to provide stents or similar means of providing structural support to an endoluminal cavity, and which may include regions of articulation and/or radiopaque markers.

A further aspect of the present invention to provide a seamless stent, or similar means of providing structural support to an endoluminal cavity.

A still further aspect of the present invention is to provide a delivery system for the inventive seamless devices, stents, occluders, filters and its use. These and other features and aspects of the invention will become more apparent in view of the following detailed description, non-limiting examples, appended claims and drawings.

BRIEF DESCRIPTION OF THE DRAWINGS

FIGS. 1A, 1B and 1C illustrate the steps of constructing a first two-dimensional frame, whereas FIGS. 1D and 1E illustrate a resulting three-dimensional shape with a filter media attached thereto.

FIGS. 2A, 2B and 2C respectively illustrate an alternate configuration of a two-dimensional frame, a resulting three-dimensional shape after annealing and a depiction of the frame with a filter media attached.

FIGS. 3A, 3B and 3C respectively illustrate an alternate configuration of a two-dimensional frame, a resulting three-dimensional shape after annealing and a depiction of the frame with a filter media attached.

FIGS. 5A, 5B and 5C respectively illustrate an alternate configuration of a two-dimensional frame, a resulting three-dimensional shape after annealing and a depiction of the frame with a filter media attached.

FIGS. 7A, 7B and 7C respectively illustrate an alternate configuration of a two-dimensional frame, a resulting three-dimensional shape after annealing and a depiction of the frame with a filter media attached.

FIG. 7D illustrates an annealed frame pattern having articulation segments in the attachment struts and FIG. 7E illustrates a frame pattern having longitudinally spaced support members interconnected by articulation segments.

FIGS. 12A, 12B, 12C, 12D and 12E respectively illustrate alternate apex and strut configurations adapted to accept and house radio-opaque markers.

FIGS. 21A and 21B respectively illustrate deployment of an occluder device in a lumen/vessel of a host and the detachment of the occluder.

FIG. 25A illustrates a delivery catheter having a guidewire lumen and guidewire supported filter.

FIGS. 25B, 25C, 25D and 25E respectively illustrate views of alternate distal catheter delivery tips.

DETAILED DESCRIPTION OF THE INVENTION

Figure 4A:
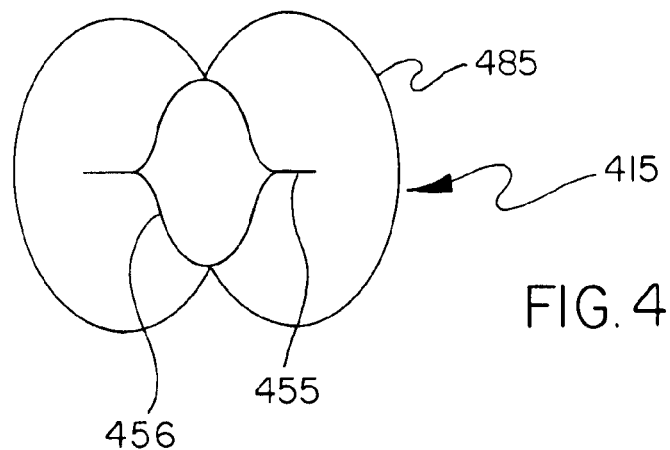
FIGS. 4A, 4B and 4C respectively illustrate an alternate configuration of a two-dimensional frame, a resulting three-dimensional shape after annealing and a depiction of the frame with a filter media attached.

As used herein the following terms are defined as followed:

The term "proximal" is defined as the location closest to the catheter hub and "distal" is the location most distant from the catheter hub. With respect to the inventive three-dimensional uni-body frame, the term "proximal" is the frame end attached to the guidewire or the frame side through which debris enters to be collected by an associated filter.

The term "uni-body" refers to a frame pattern formed from a single piece of material and therefore considered "seamless."

Terms such as unitary, integral, one-piece are synonymous with "uni-body" and also refer to a frame pattern that is formed from a single or common piece of material.

Filament, wire or ribbon are alternate terms used to describe the portions/sections of pattern material that remain after etching a planar precursor frame material and form the attachment struts, the support struts, the filter/filter support struts that extend in the longitudinal, circumferential, or any other direction necessary to define a frame pattern.

FIGS. 1A-1D schematically show the four method steps that are followed to manufacture a uni-body, self-expanding filter device in accordance with the present invention. FIG. 1A shows a flat sheet material 110, preferably a shape memory alloy material, e.g., a NiTi alloy, Nitinol, or any other suitable bioacceptable material, such as a metal, e.g., stainless steel, or bioacceptable polymer. The flat sheet material 110 is used to form the "uni-body" frame pattern 115 of FIG. 1C, or other frame patterns described hereinafter.

A desired pattern is formed on sheet material 110, as in the case of FIG. 1B, which shows a radially symmetric filter frame pattern having six "pie" shaped wedges 120. The wedges 120 are removed by etching in a chemical photo-etching process, or any other suitable technique, to form a frame defined by filament sized material. The frame pattern can also be obtained by using a laser or any other cutting procedure or process capable of precisely etching, stamping, or otherwise cutting the flat sheet 110 into the preferred shape.

Radial sides 125,130 and arcuate side 135 circumscribe the wedges 120. Slits 145 are formed and center section 150 is removed by any suitable cutting technique. After the slits 145 are formed, and wedges 120 and center section 150 removed, flashing 140 is removed (such as by trimming with fine scissors or diagonal cutters), leaving the desired skeletal two-dimensional filter frame/pattern 115, shown in FIG. 1C.

Skeletal frame 115 includes attachment struts 155 with proximal ends 165 that are to be fixed or attached to proximal connecting member 170 of FIG. 1D, adapted to cooperate with a guidewire (not shown). Attachment struts 155 extend seamlessly from support struts 156 because they are formed from the same precursor material. Support struts 156 are seamlessly connected to or seamlessly interconnected with one another. Seamlessly interconnected support struts 156 define a boundary, perimeter or cell having the configuration of a six-pointed "star." When frame 115 is converted into a three-dimensional configuration, the seamlessly associated/interconnected struts 156 typically form a "closed" support member 156A that circumscribes the longitudinal axis of the three-dimensional frame, thereby providing a radial or transverse dimension to the three-dimensional frame. The boundary, perimeter, cell or support member 156A can be any geometric configuration so long as it provides a radial dimension (transverse to the longitudinal axis) for the frame. The support member circumscribes the longitudinal axis of the frame and may also be described as being ring-shaped. In addition to providing the frame with a radial dimension, as shown in FIG. 1D, the support member 156A is typically the location for attaching the proximal open end 161 of the filter 160. Thus the support member also functions to maintain the proximal end of filter media 160 in the open operative configuration. Filter media 160 may be formed from any suitable material, and also includes a closed distal end 162.

The planar, two-dimensional frame pattern of FIG. 1C is then annealed, normally by thermal annealing, into a three-dimensional configuration. The three-dimensional annealed frame configuration 175, may be further processed, as described hereinafter, to include a filter media resulting in filter 100 which includes the frame 175 and filter media 160, as in FIGS. 1D and 1E. For ease of consistency and brevity throughout the remainder of the application and without relinquishing equivalents thereof, Nitinol is used as the filter frame material in each and every embodiment shown and described hereinafter. However, as discussed above, other suitable materials, such as, titanium nickel alloys, shape memory materials, biocompatible metals, e.g., stainless steel, or plastic may be used for the uni-body filter frame.

FIGS. 2A-2C through 11A-11C depict alternate filter frame patterns that can be formed following the procedures described with reference to FIGS. 1A-1E. As a result, the various struts are seamlessly interconnected since they are formed from the same precursor material.

FIG. 2A illustrates a plan view of an alternate frame pattern 215 having hoop shaped struts 256 connected to attachment struts 255. FIG. 2B illustrates the three dimensional filter frame 275 after annealing with proximal ends of the attachment struts 255 fixed to the proximal connecting member 270 and struts 256 seamlessly connected to one another and forming a closed support member 256A. As with FIG. 1C, struts 255 seamlessly extend from support member 256A. FIG. 2C illustrates a filter 200 attached to a guidewire 280. The filter 200 includes the three-dimensional frame 275 with a filter media 260 having a "butterfly" configuration. The configuration of filter media 260 can also be described as substantially parabolic.

FIG. 3A illustrates an alternate two-dimensional (plan view) frame pattern 315 having attachment struts 355, attachment strut proximal ends 365, filter struts 385 which may also support optional filter media 360 of FIG. 3D. Filter pattern 315 also includes support struts 356. Support struts 356 and filter struts 385, which are seamlessly associated with one another, cooperate to define cell 357, which is configured in the shape of a diamond. Struts 355, 356 and 385 are seamlessly associated with one another since they are formed from the same precursor material. Struts 356 define a boundary around six cells 357 and form a closed support member 356A for maintaining the three-dimensional filter of FIG. 3C in an open, operative configuration. FIG. 3B illustrates three-dimensional frame 375 that is obtained after the two dimensional filter frame pattern is annealed, with the proximal ends 365 of the attachment struts 355 fixed to proximal connecting member 370. In the embodiment of FIG. 3B, the filter struts 385 allow the device to be used as a filter, without the filter media shown in FIG. 3C. While the filter pattern of FIG. 3B shows six filter struts 385, any number of filter struts or support struts can be used, including, but not limited to 4, 5, 7, 8, 9, 10, 11, 12, etc. In addition, although FIG. 3A depicts the filter frame 315 with diamond shaped cells/openings 357, cells 357 can be of any geometrical shape or size, so long as the openings are of sufficient size to permit blood flow and/or filtering. FIG. 3C illustrates the annealed filter frame pattern of FIG. 3B with filter media 360 attached to a guidewire 380.

Figure 4B:
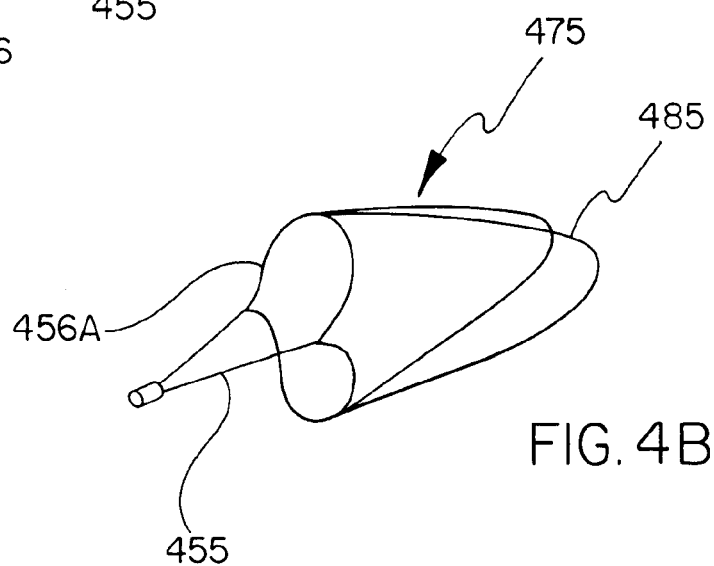
Figure 4C:
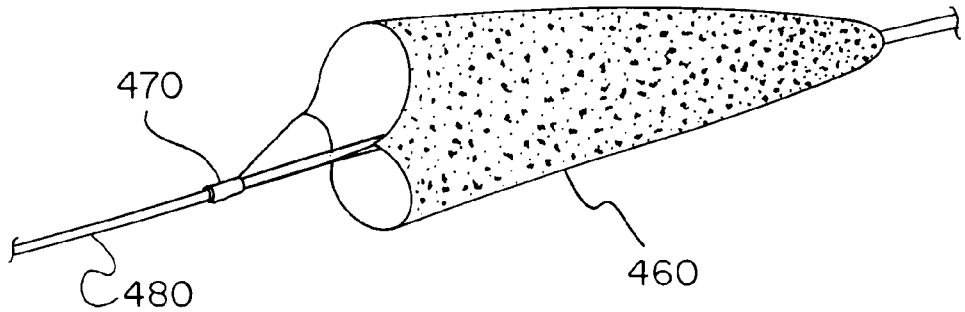

FIG. 4A illustrates a two-dimensional alternate seamless frame pattern 415 having attachment struts 455, support struts 456, and filter/filter media support struts 485. The pattern is seamless because it is formed from the same precursor material. FIGS. 4B and 4C illustrate three-dimensional views of filter frame pattern 475 after annealing, with the proximal ends of the attachment struts 455 fixed to the proximal connecting member 470, support struts 456 forming support member 456A, and filter media support struts 485 extending in a distal direction. FIG. 4C illustrates the annealed filter frame pattern 475 of FIG. 4B with filter media 460 attached to a guidewire 480.

FIG. 5A illustrates the two-dimensional alternate seamless filter pattern 515 having attachment struts 555, support struts 556, filter media support members 590, and filter support struts 585. The pattern is seamless because it is formed from the same precursor material. FIGS. 5B and 5C illustrate three-dimensional views of the filter frame pattern 515 of FIG. 5A after annealing, frame 575, with proximal ends of the attachment struts 555 fixed to the connecting member 570, support struts 556 of FIG. 5A form closed support member 556A, and filter media support struts 585 extend distally away from the proximal connector 570. FIG. 5C illustrates the annealed filter frame pattern 575 of FIG. 5B with filter media 560 attached to a guidewire 580.

Figure 6A:
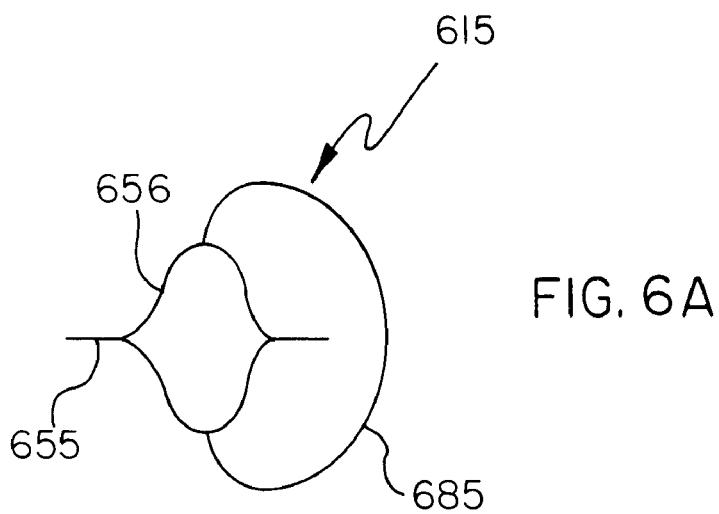
FIGS. 6A, 6B and 6C respectively illustrate an alternate configuration of a two-dimensional frame, a resulting three-dimensional shape after annealing and a depiction of the frame with a filter media attached.
Figure 6B:
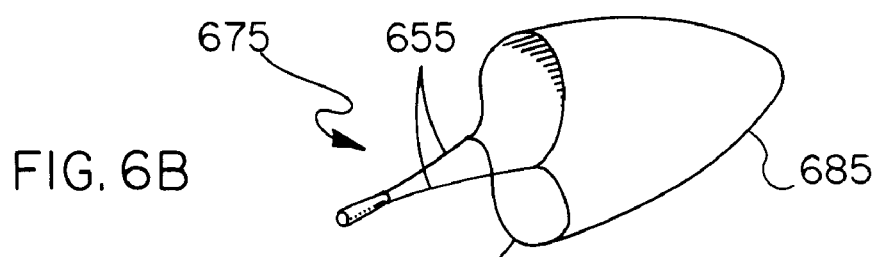
Figure 6C:
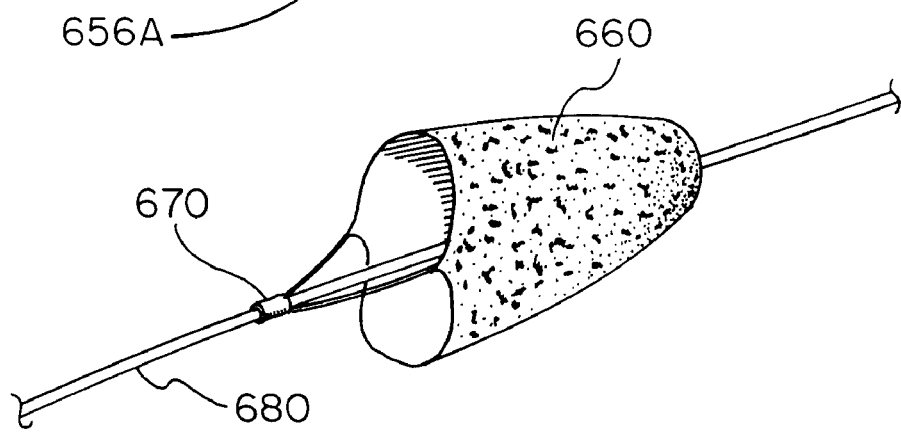

FIG. 6A illustrates the two-dimensional alternate seamless filter pattern 615 having attachment struts 655, support struts 656 and filter support struts 685. The pattern is seamless because it is formed from the same precursor material. FIGS. 6B and 6C illustrate three-dimensional views of filter frame pattern 615 of FIG. 6A after annealing, with the proximal ends of the attachment struts 655 fixed to the connecting member 670, support struts 656 of FIG. 6A forming support member 656A and filter media support struts 685. FIG. 6C illustrates the annealed filter frame pattern 675 of FIG. 6B with filter media 660 attached to a guidewire 680.

FIG. 7A illustrates a two-dimensional view of a seamless alternate filter pattern 715 having attachment struts 755 and support member struts 756. The pattern is seamless because it is formed from the same precursor material, for supporting the open end of filter media 760 of FIG. 7C. FIGS. 7B and 7C illustrate side views of the three-dimensional filter frame 775, after annealing, with the proximal ends of the attachment struts 755 fixed to the connecting member 770 and support struts 756 of FIG. 7A forming support member 756A. FIG. 7C illustrates the annealed filter frame pattern of FIG. 7B with filter media 760 attached to a guidewire 780. FIG. 7D illustrates the annealed frame pattern having articulation segments 790 in the attachment struts 755. FIG. 7E illustrates an alternate design, wherein there are two longitudinally spaced support members 756A seamlessly interconnected to one another by articulation segments 790, described in greater detail hereinafter.

Figure 8A:
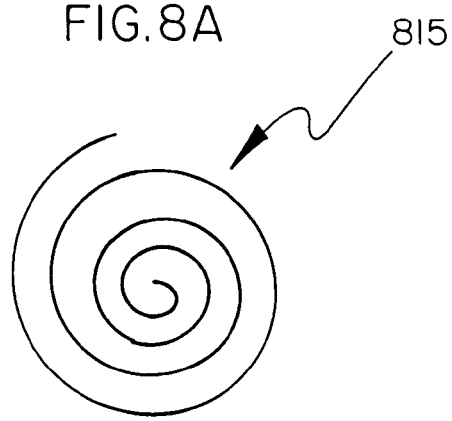
FIGS. 8A, 8B and 8C respectively illustrate an alternate configuration of a two-dimensional frame, a resulting three-dimensional shape after annealing and a depiction of the frame with a filter media attached.
Figure 8B:
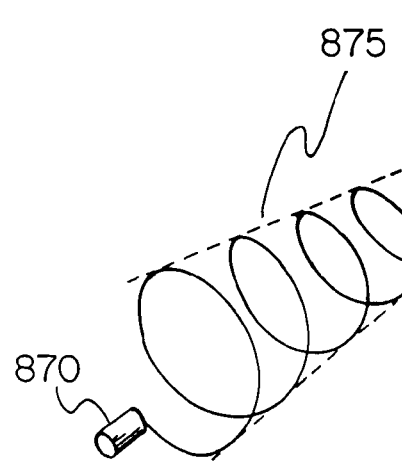
Figure 8C:
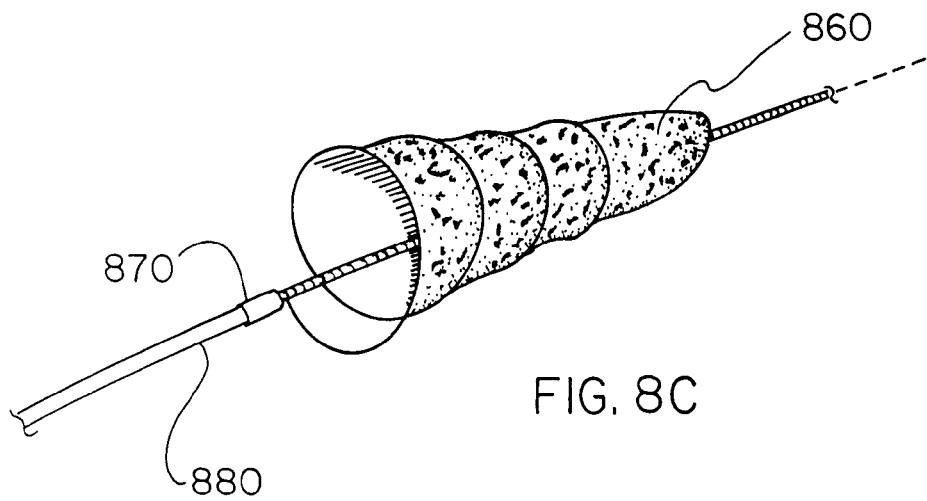

FIG. 8A illustrates a two-dimensional view of an alternate spirally configured filter pattern 815. FIGS. 8B and 8C illustrate three-dimensional views of the filter frame pattern 815 of FIG. 8A after annealing, frame 875, with a proximal end of the frame 875 fixed to the connecting member 870. FIG. 8C illustrates the annealed filter frame pattern of FIG. 8B with filter media 860 attached to a guidewire 880. In the filter frame illustrated in FIG. 8B, one of the turns of the spirally shaped frame, which is not "closed," forms the support member that provides radial dimension to the frame.

Figure 9A:
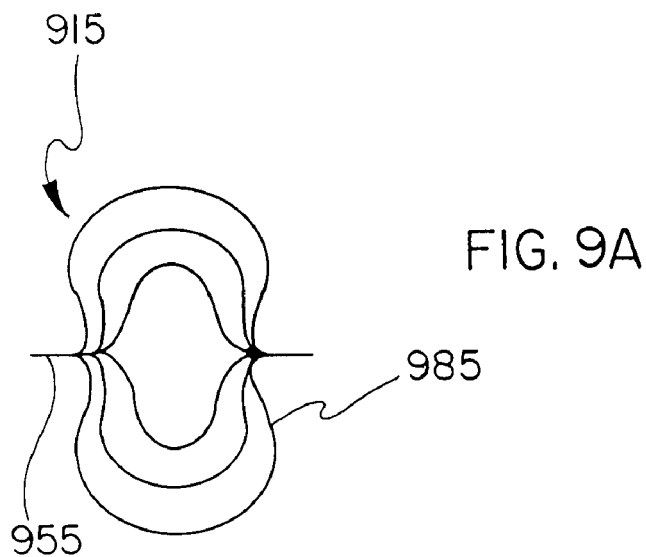
FIGS. 9A, 9B and 9C respectively illustrate an alternate configuration of a two-dimensional frame, a resulting three-dimensional shape after annealing and a depiction of the frame with a filter media attached.

FIG. 9A illustrates a two-dimensional view of an alternate seamless filter pattern 915 having attachment struts 955 and filter media support struts 985. The pattern is seamless because it is formed from the same precursor material. FIGS.

Figure 9B:
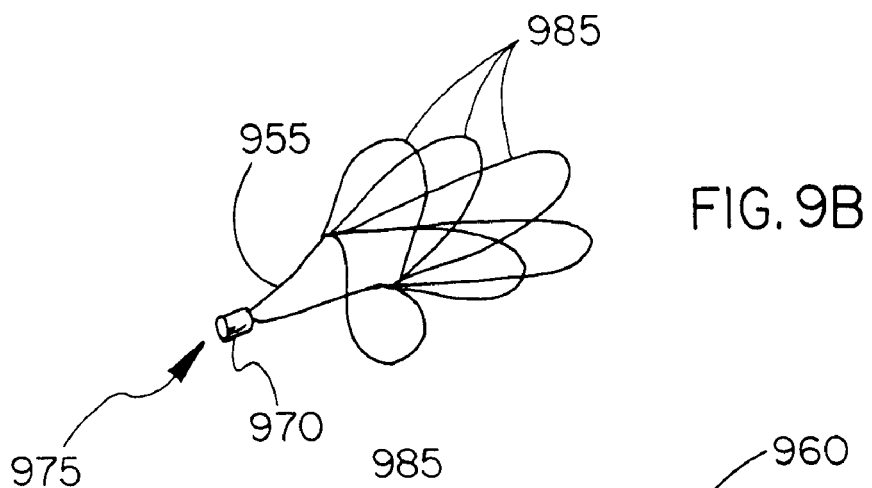
Figure 9C:
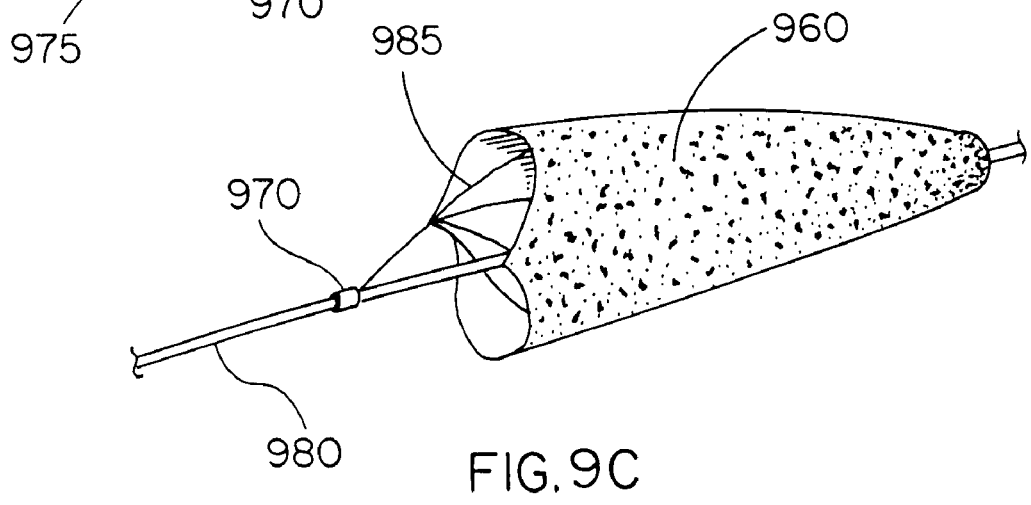

9B and 9C illustrate three-dimensional views of the filter frame pattern after annealing, frame 975, with the proximal ends of the attachment struts 955 fixed to the proximal connecting member 970. In this embodiment the filter media support struts 985 closest to the proximal connector also function as the closed support member described herein to provide the transverse dimension of the frame and support the proximal end of the filter 960. FIG. 9C illustrates the annealed filter frame pattern 975 of FIG. 9B and filter media 960 attached to a guidewire 980.

Figure 10A:
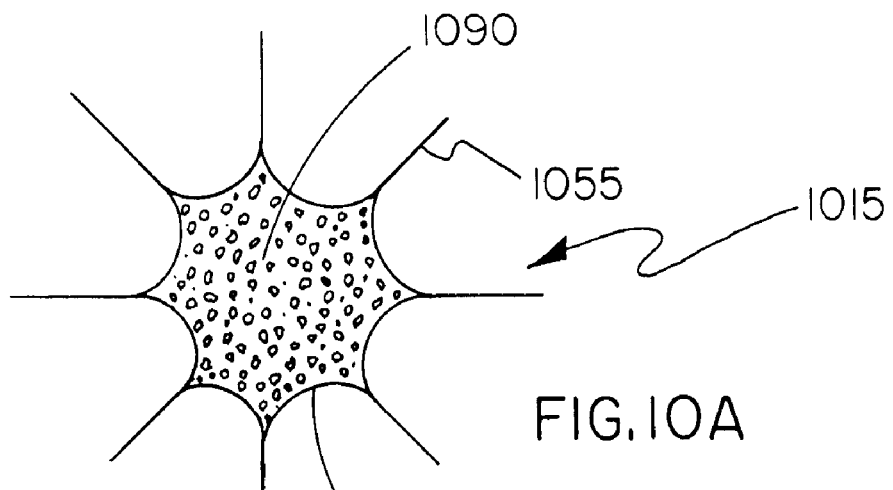
FIGS. 10A, 10B and 10C respectively illustrate an alternate configuration of a two-dimensional frame, a resulting three-dimensional shape after annealing and a depiction of the frame with an integral filter media.
Figure 10B:
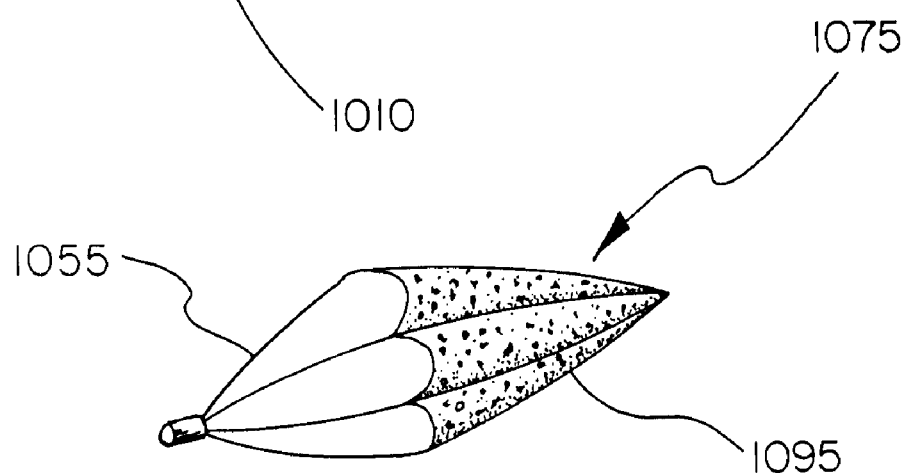
Figure 10C:
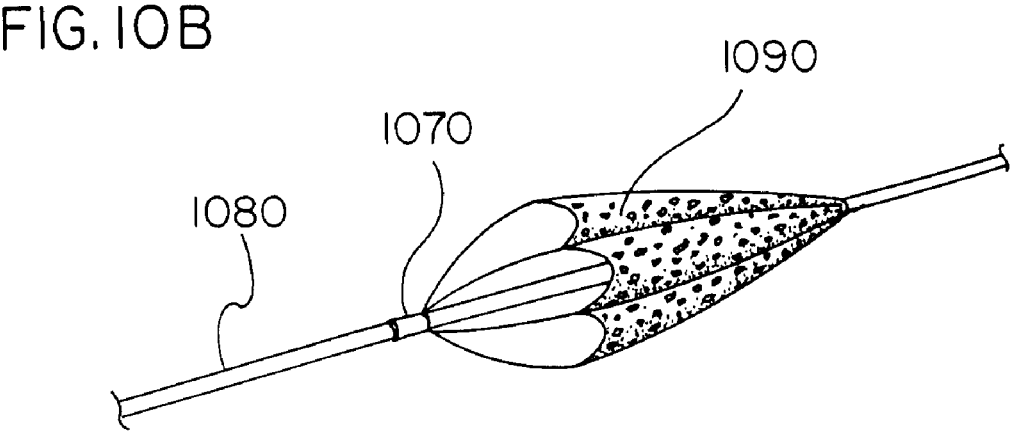

FIG. 10A illustrates a two-dimensional view of an alternate seamless filter pattern 1015 having attachment struts 1055 and a central portion of the planar Nitinol precursor material 1010 rendered porous 1090. FIGS. 10B and 10C illustrate three-dimensional views of the filter frame pattern 1015 of FIG. 10A after annealing, frame 1075, with the proximal ends of the attachment struts 1055 fixed to the connecting member 1070, and the porous precursor material 1090 having pleats 1095. FIG. 10C illustrates the annealed filter frame pattern 1075 of FIG. 10B attached to a guidewire 1080. A separate filter media is not necessary in the embodiment illustrated in FIGS. 10A-10C because the porous precursor portion 1090 serves as the filter media.

Figure 11A:
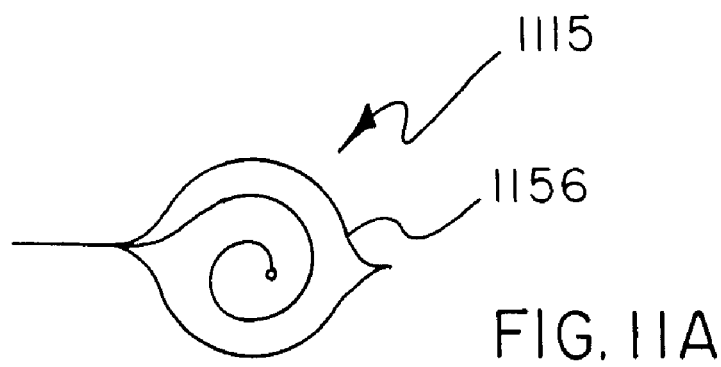
FIGS. 11A, 11B and 11C respectively illustrate an alternate configuration of a two-dimensional frame, a resulting three-dimensional shape after annealing and a depiction of the frame with a filter media attached.
Figure 11B:
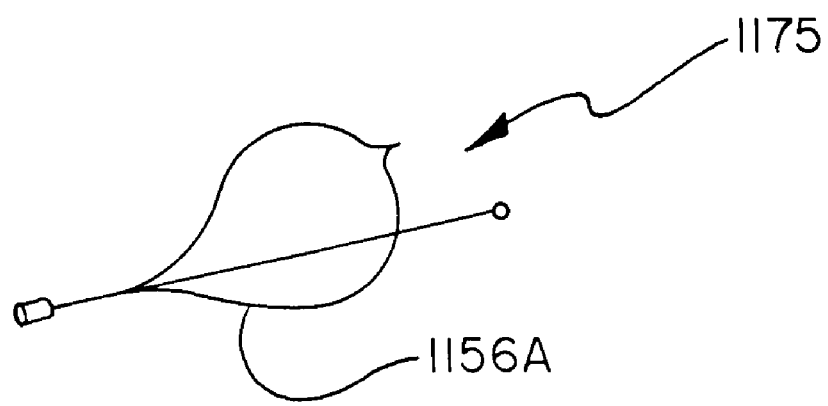
Figure 11C:
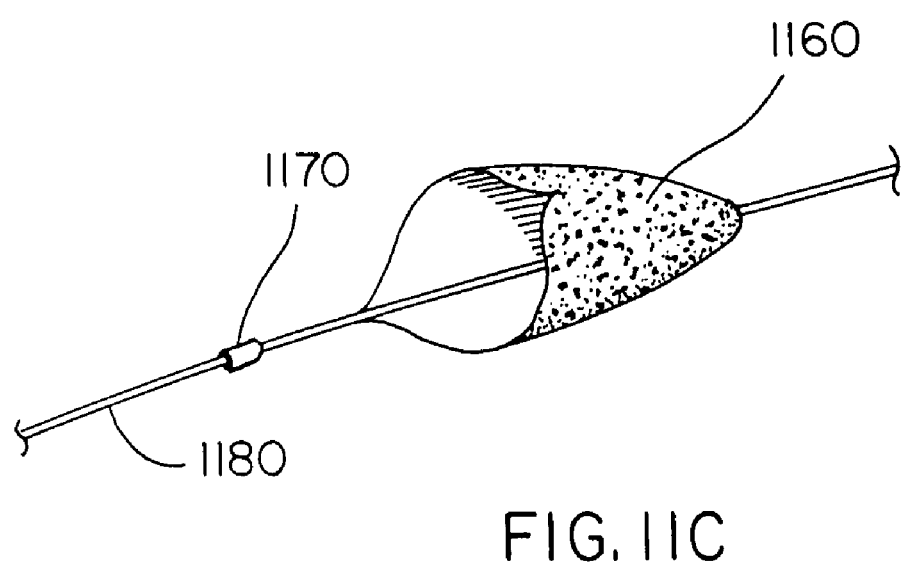

FIG. 11A illustrates a two-dimensional view of an alternate seamless filter pattern 1115 having attachment and filter strut 1156 which will also function as the closed support member 1156A shown in FIG. 11B. FIGS. 11B and 11C illustrate three-dimensional views of the filter frame pattern 1115 of FIG. 11A after annealing, frame 1175, with the proximal end of the closed support member 1156A fixed to the connecting member 1170. FIG. 11C illustrates the annealed filter frame pattern 1175 of FIG. 11B with filter media 1160 attached to a guidewire 1180.

Although the above embodiments show a single support member 156A, 256A, 356A, 456A, 556A, 656A, 756A, 956A, etc., it is clearly within the scope of the invention to have a plurality of longitudinally spaced support members, i.e., members that circumscribe the longitudinal axis of the frame, that are seamlessly interconnected with one another via struts or articulation segments, as in FIG. 7E. Similarly other embodiments described hereinafter may also include a plurality of seamlessly interconnected support members where the mechanism for interconnection includes struts, and/or the articulation segments which are defined hereinafter. In addition, when there are more than two support members connected to one another, some or all may be interconnected with struts and some or all may be interconnected via articulation segments. Thus, there could be a series of two, three, four or more members, and in the case with at least three support members that circumscribe the pattern's longitudinal axis, both struts and articulation segments can be used in an alternating pattern.

FIGS. 12A, 12B, 12C, 12D and 12E illustrate alternate configurations of stent strut, and apex designs which allow for, accept and house ancillary components. FIG. 12A depicts a housing 1210, which could be machined, stamped, lasered or etched into the stent frame. Housing 1210 is then filled with a material 1250 such as gold or platinum-iridium (to provide enhanced radio-opacity) or with a therapeutic agent such as a drug (to provide a prescribed biological response). FIG. 12B depicts housing 1210 located along the side of a strut. FIG. 12C depicts multiple housings 1210 along a strut. FIG. 12D depicts multiple housings 1210 located within the strut periphery. FIG. 12E depicts an alternate shape (arrowhead) housing 1210 (to be used as a radiopaque marker housing) located within the strut periphery. It should be noted that multiple shapes and sizes of housings could be configured. The radiopaque markers could be located in any strut or support member of the frame of the filter or the stent. Advantages of the application of radio-opaque markers in the fashions shown are: 1) stent cross section thickness is not increased (lending to reduction in introductory device profiles), 2) allows for precise and uniform spacing of markers, and 3) allows for a multitude of shapes (dots, arrows and other characters such as letters or words) to be easily incorporated into the frame. The housings may also provide a cavity in which to insert and/or attach onboard electronics or sensors.

Figure 13:
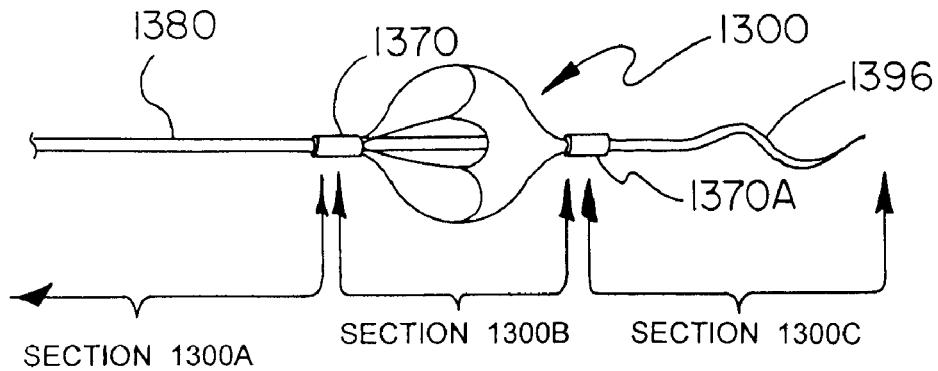
FIG. 13 illustrates a three-dimensional frame with an attached filter media positioned between a guidewire and an atraumatic tip.

FIG. 13 illustrates an embolic filter assembly system 1300 that includes three functionally distinct regions. Section 1300A includes a support wire that terminates at its distal end in connecting member 1370. The support wire may be the guidewire 1380 used to deliver a therapeutic device, e.g., a deployment catheter or angioplasty balloon. Section 1300B is any one of the embolic filter devices described in FIGS. 1A-1E through 11A-11C described herein, or another other device described hereinafter. Section 1300C may include an atraumatic tip 1396 or other suitable tip known to those skilled in the art having a proximal end fixed/attached/cooperating with distal connecting member.

Figure 14A:
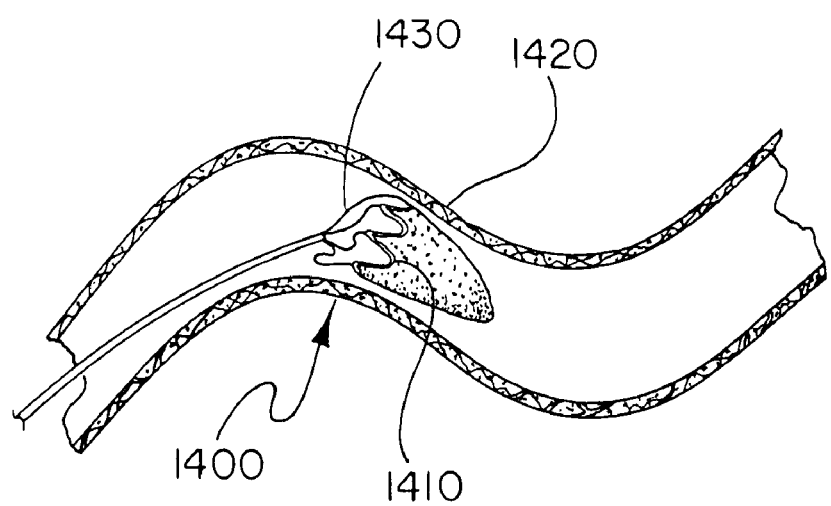
FIGS. 14A and 14B depict the filtering apparatus as deployed within a vessel having tortuous anatomy.

FIG. 14A depicts the filter apparatus 1400 as deployed in a vessel 1420 with tortuous anatomy. As shown, such a condition results in a non-linear apparatus deployment configuration. In order for filter frame 1410 to maintain sufficient vessel wall apposition (which eliminates peri-device channel formations), the tether elements 1430 must be capable of deforming and/or articulating.

Figure 14B:
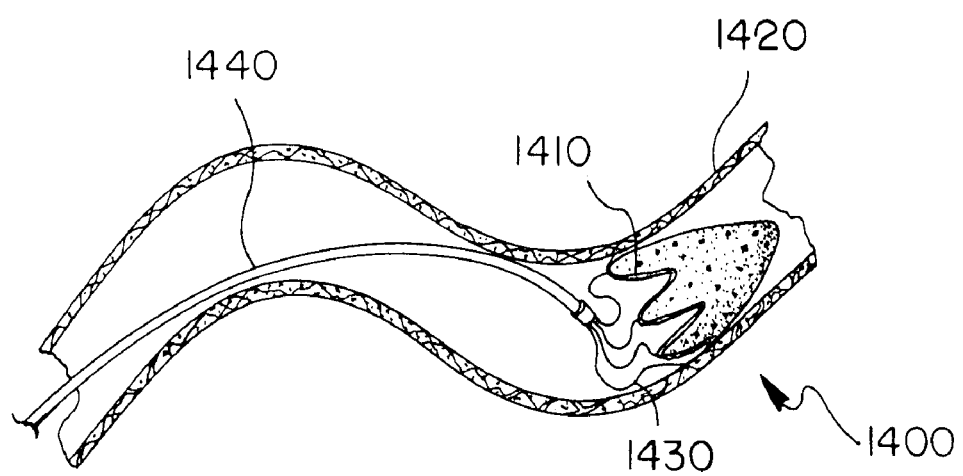

FIG. 14B depicts the filter apparatus 1400 as deployed at a different site within the same vessel 1420 anatomy of FIG. 14A, once again demonstrating the flexibility required of the deflecting and articulating tether elements 1430. It is clear in this depiction that the guidewire 1440 does not necessarily follow the host vessel centerline. This phenomenon, coupled with anatomical variances and the requirement of complete vessel wall apposition of the filter frame 1410 makes the inclusion of articulating tether elements 1430 a benefit and necessity for safe and confident embolic protection of downstream vasculature.

Figure 15:
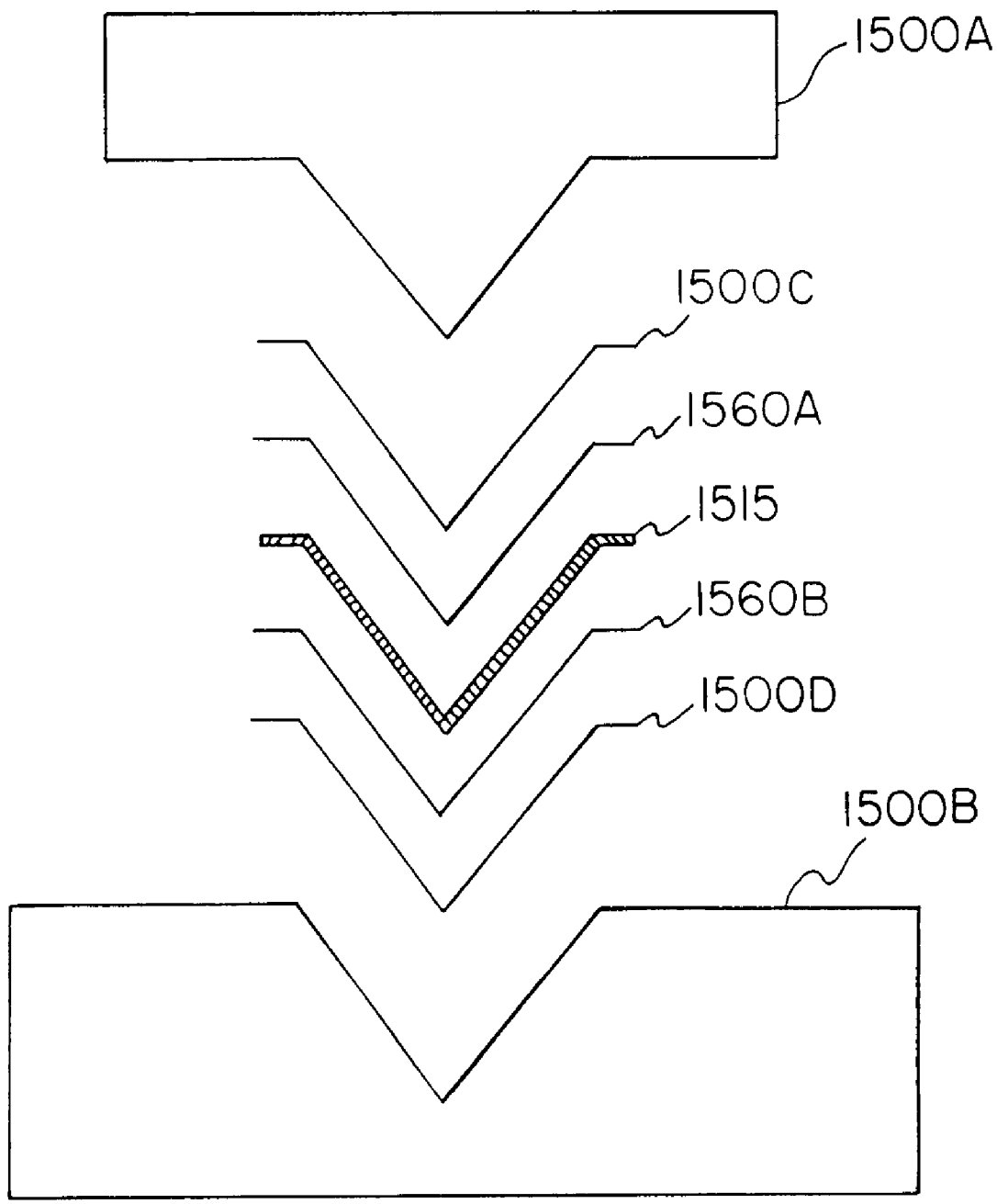
FIG. 15 illustrates an alternate system for assembling an alternate embolic filter configuration.

FIG. 15 illustrates an arrangement to attach a filter media to any of the annealed filter frames described herein. The frame 1515, is sandwiched between filter media portions 1560A and 1560B, which are respectively sandwiched between cushion elements 1500C and 1500D, which layered assembly is located between heated top plate 1500A and heated base plate 1500B. Thus, resulting three-dimensional lamination of FIG. 15 has a cross-sectional view that is substantially conical. Application of heat and pressure, via heated platens 1500A and 1500B, result in the integral bonding of the filter media 1560A and 1560B, and the interposed frame 1515. The filter frame configuration via the lamination procedure depicted in FIG. 15 results in a filter assembly configuration resembling a "butterfly net."

Figure 16:
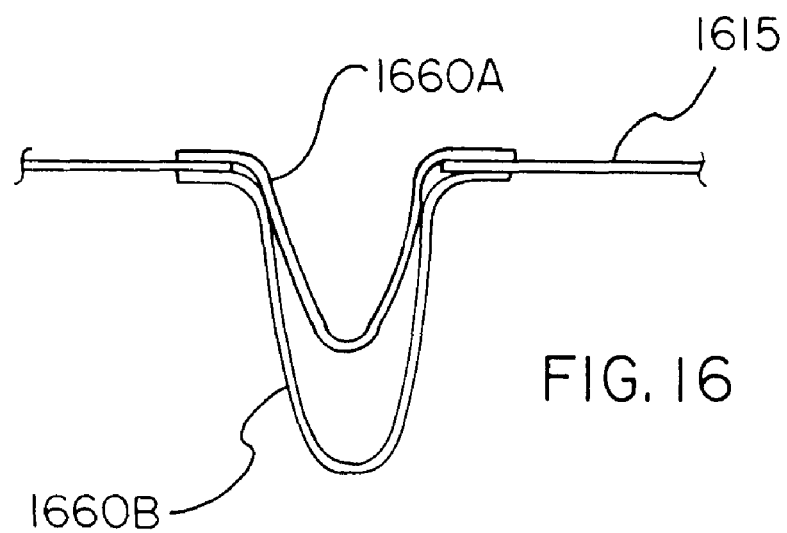
FIG. 16 illustrates a system for assembling a filter-in-filter device.
Figure 16A:
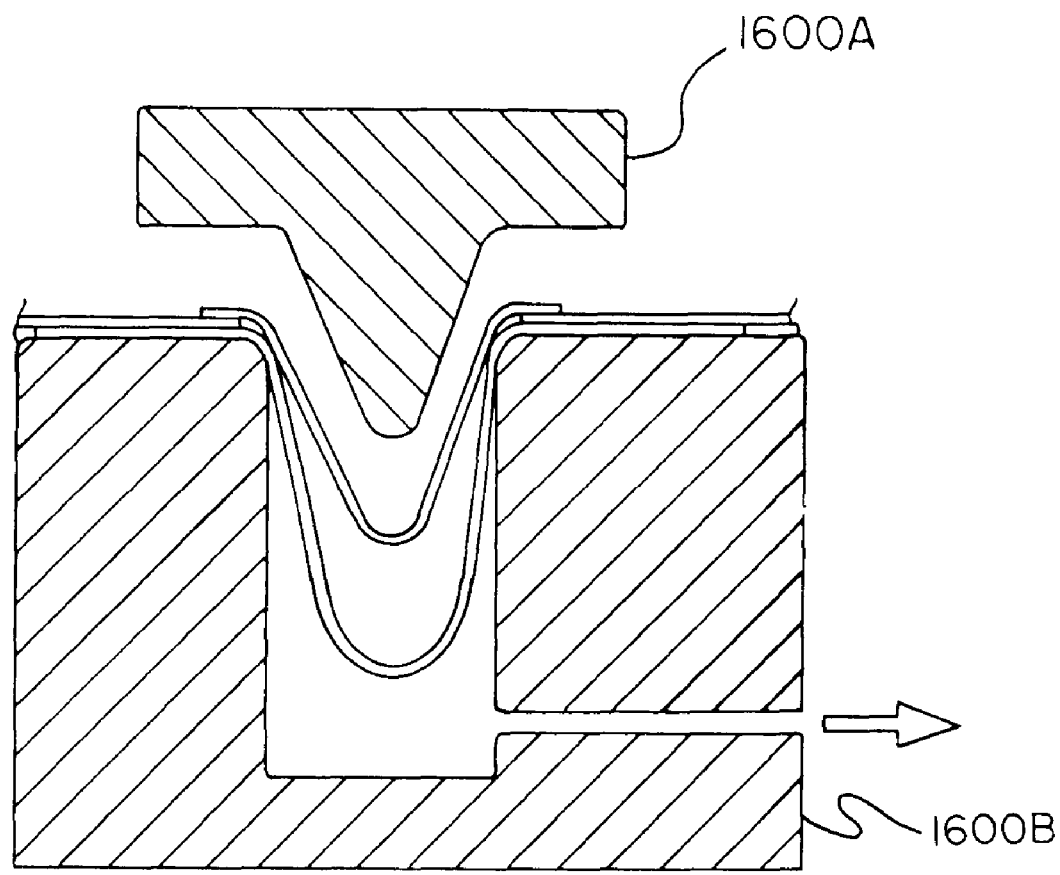

FIG. 16 schematically shows an alternate procedure for attaching filter media to an annealed filter frame. In FIG. 16, an annealed filter frame 1615 is sandwiched between adjacent laminae of inner filter media 1660A and outer filter media 1660B. Heat and pressure are applied via upper and lower punch and die platens 1600A and 1600B. The application of heat and pressure results in an integral bonding of the filter media 1660A and 1660B and interposed frame 1615. During the heating and pressure lamination process, a vacuum may be applied in the lower platen 1600B thereby bonding the filter media and skeletal filter frame together. The filter media shown in FIG. 16 is normally interposed only within the immediate vicinity of the filter frame 1615. Additionally, the application of the vacuum can be used to optimize the filter frame geometry. The method shown in FIG. 16 can produce a filter frame configuration that resembles a butterfly net, such as the one shown in the device of FIGS. 7A-7C. This method can also be used to produce a frame-supported "filter-in-filter," which is shown in further detail in FIG. 17, described below.

Figure 17:
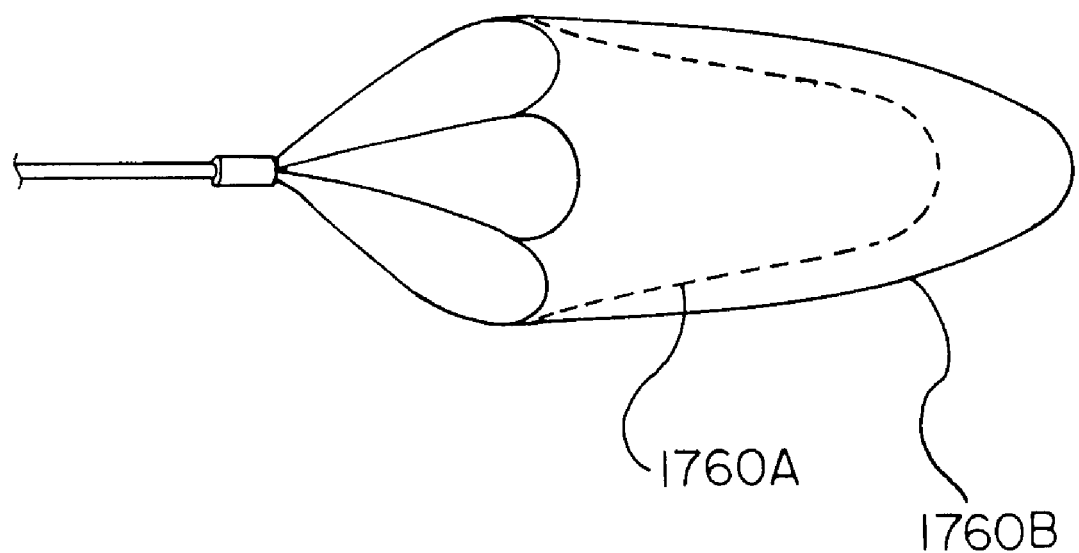
FIG. 17 illustrates the filter-in-filter assembled using the system of FIG. 16.

FIG. 17 shows an alternate embodiment of the present invention incorporating a two stage "filter-in-filter" design. The filter-in-filter design will provide improved filtration efficiencies, such as allowing each filter lamina to have a different porosity by using an inner filter media 1760A and an outer filter media 1760B. Alternatively, either filter media 1760A or 1760B can incorporate an integral Nitinol frame as one of the filter members. Alternatively still, both the inner and outer filter media 1760A and 1760B could be an integral Nitinol filter frame. Use of an uni-body Nitinol frame, such as those described herein, would provide additional structural benefits in the completed filter frame apparatus.

Figure 18A:
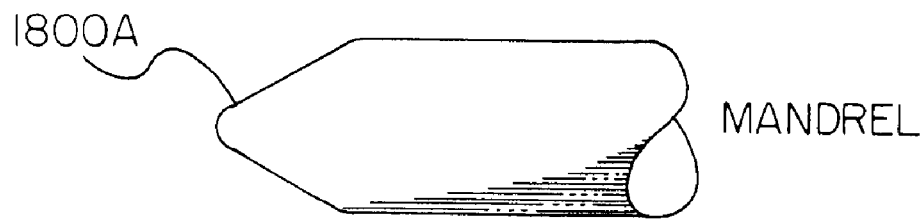
FIGS. 18A, 18B and 18C respectively illustrate a tooling device, a two-dimensional frame being formed into a three-dimensional configuration, and the tooling device supporting the three-dimensional frame for annealing.
Figure 18B:
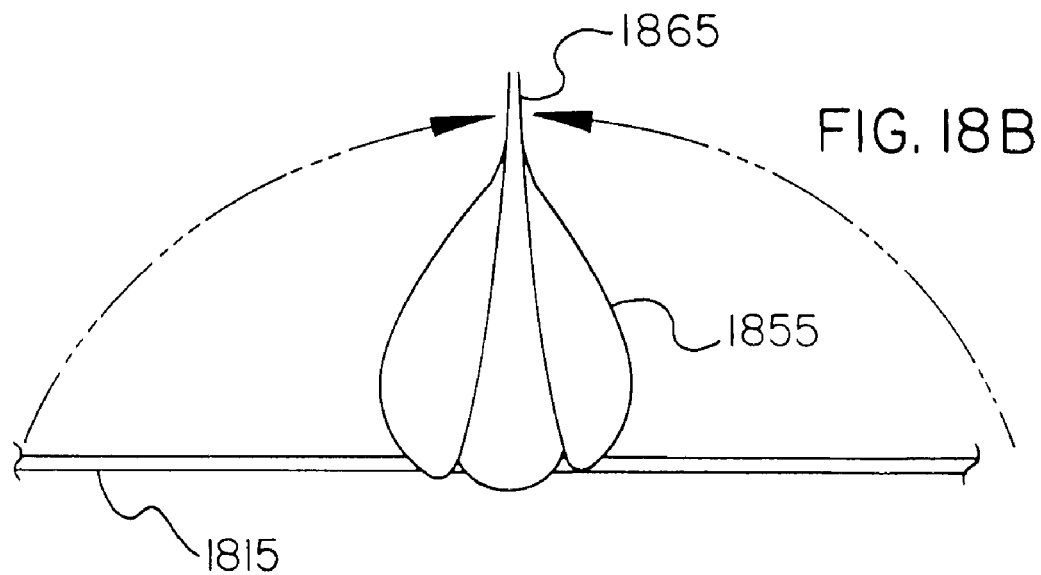
Figure 18C:
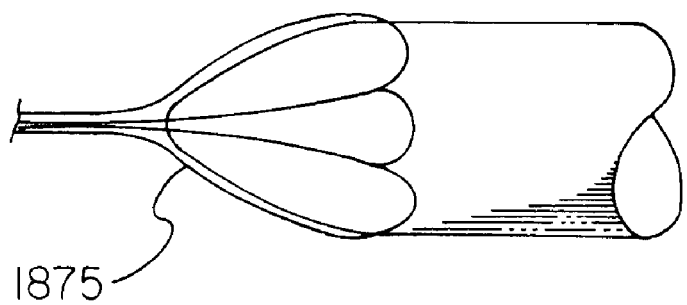

FIGS. 18A, 18B, and 18C schematically illustrate an annealing method in which a planar, two-dimensional filter frame is converted into a three-dimensional configuration with the use of an appropriate fixturing/tooling device, e.g., a mandrel. Mandrel 1800A, shown in FIG. 18A, is used to form the filter frame 1815 of FIG. 18B into the desired shape. After cutting a flat metal sheet into the desired two dimensional configuration, such as that described above, the proximal ends 1865 of attachments struts 1855, i.e., the endpoints of the two-dimensional filter frame 1815, are collected at a point along the axis of radial symmetry as shown in FIG. 18B. As depicted in FIG. 18C, the filter frame 1815 is placed onto the fixturing device, which, in this case, is the mandrel 1800A of FIG. 18A to impart a defined, three-dimensional configuration, and the frame 1815 of FIG. 18B is annealed to preserve the desired configuration. After annealing, the three-dimensional filter frame 1875 can be elastically deformed into its original two-dimensional shape where a filter media can be applied according to any of the methods described and illustrated herein. Following the attachment of the filter media, the three-dimensional filter configuration is readily obtained.

Figure 19A:
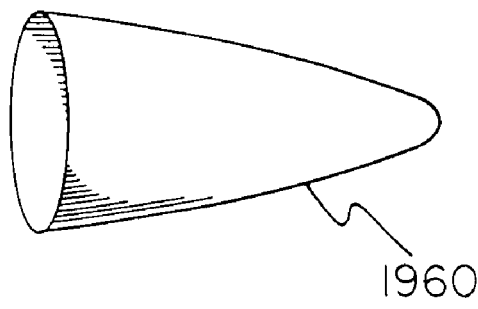
FIGS. 19A, 19B and 19C respectively illustrate the steps for converting a conical filter into "sombrero" shaped filter configuration.
Figure 19B:
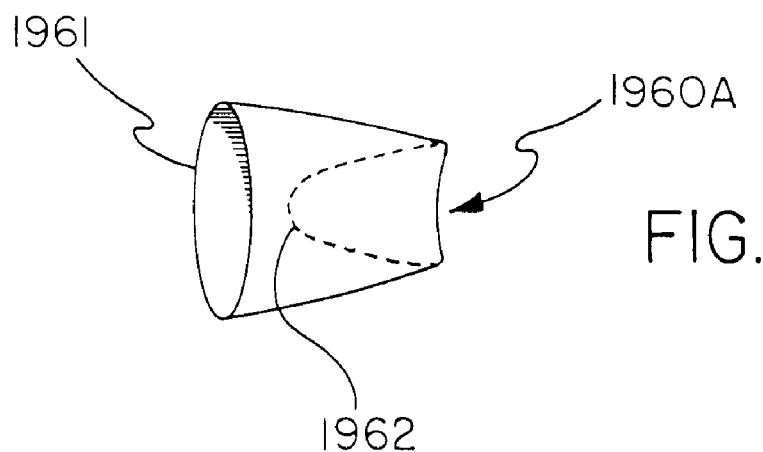
Figure 19C:
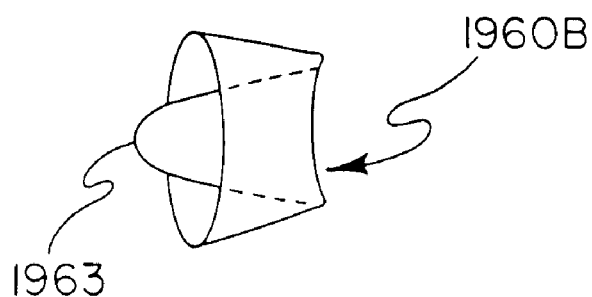
Figure 19D:
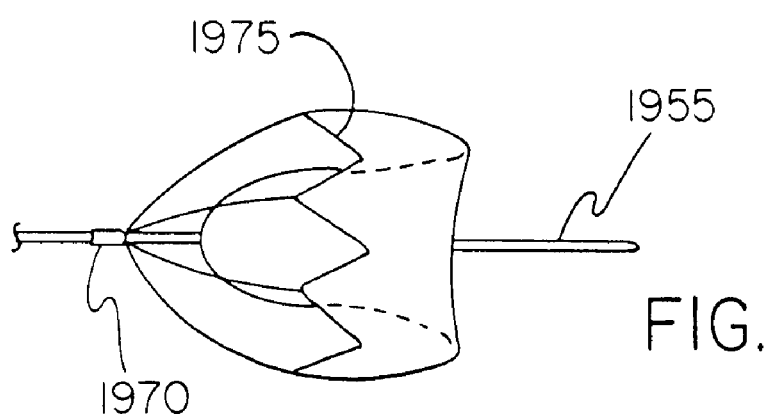
FIG. 19D illustrates a three-dimensional frame supporting a "sombrero" shaped filter media.

FIGS. 19A, 19B, 19C and 19D illustrate an alternate filter configuration using a "sombrero" shaped filter media 1960B with a supporting frame. To form the sombrero frame and filter shown in FIG. 19D, a conical filter 1960, as shown in FIG. 19A, has its closed distal end 1962 inverted toward the open proximal end 1961 of the conical filter 1960, to form a convex, hat-like base as shown in FIG. 19B. This inversion shortens the filter length, but retains the original area of the filter element 1960. Next, the convexity is increased until the apex 1963 extends beyond the open end 1961, as shown in FIG. 19C. The filter 1960 thus has been shortened further, but the effective filter area still remains identical to the original conical filter area. The sombrero filter 1960B is attached to frame 1975, FIG. 19D. The frame includes attachment struts that are fixed to a connecting member 1970, which in turn is cooperatively associated with a guidewire 1955. Compared to conventional conical filter frame designs, the sombrero filter frame allows more surface area per unit length, or, alternatively, reduces filter length without compromising filter surface area and deflection of the trapped debris away from the vessel centerline. The desired sombrero filter frame configuration will also increase the reliable removal of entrapped debris.

Figure 19E:
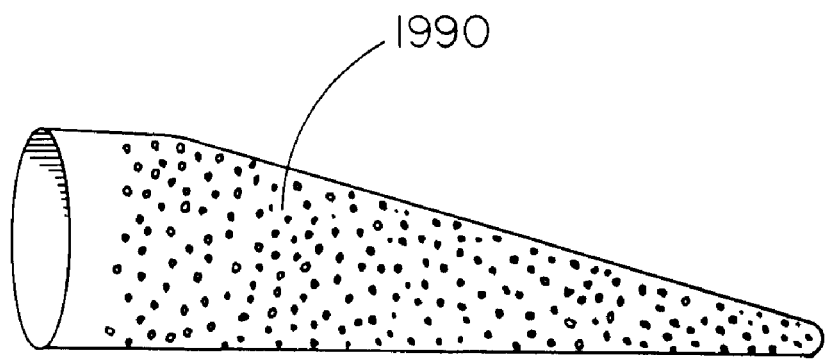
FIGS. 19E and 19F depict an alternative filter sack configuration in which the sack resembles an asymmetric cone.
Figure 19F:
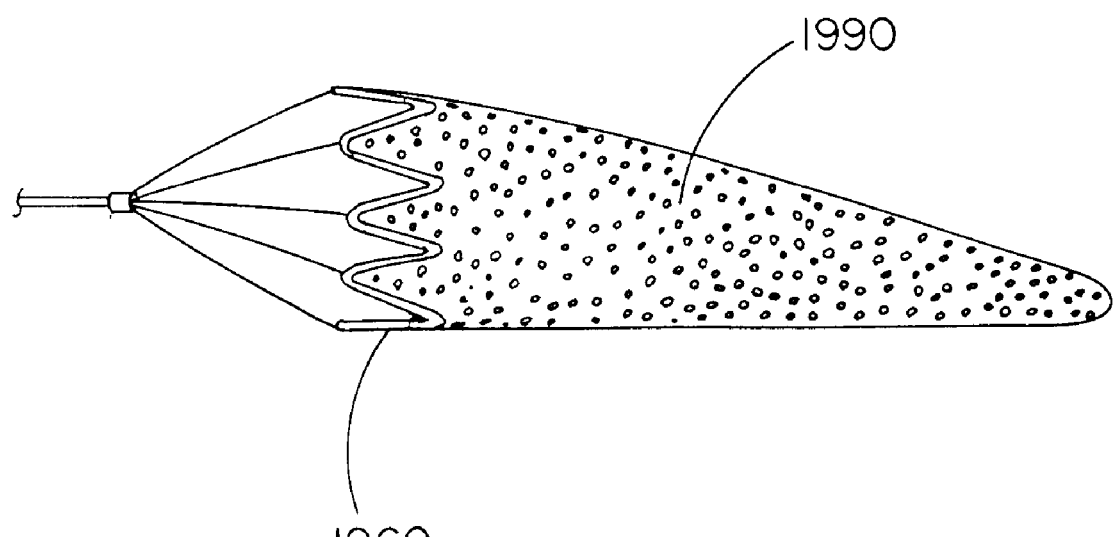

FIGS. 19E and 19F depict an alternate filter sack configuration, also designed to collect and hold embolic debris away from the vessel centerline. In this case, an asymmetric cone shaped filter media sack 1990 is produced and attached to the filter frame 1960. Collected emboli will tend to collect at the tip of the sack 1990 and are held offset in the vessel, thus allowing relatively unperturbed flow at the vessel centerline.

Figure 20A:
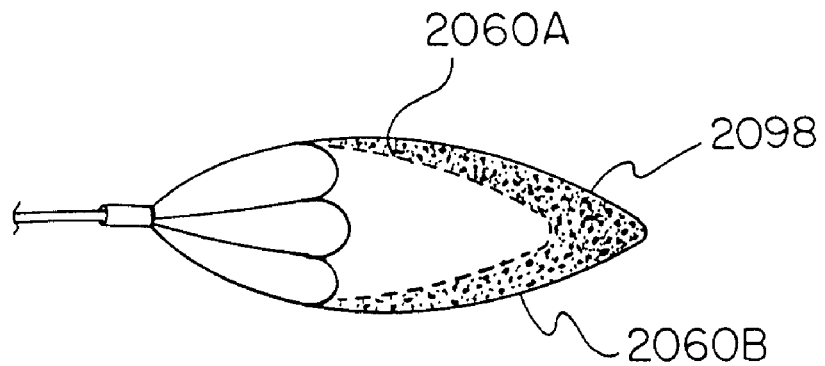
FIGS. 20A, 20B and 20C respectively illustrate a filter-in-filter configuration with a pharmacological agent loaded in the space between the filter media, an alternate filter configuration with the filter media pre-loaded with the pharmacological agent, and the elution of the pharmacological agent in a lumen/vessel of a host.
Figure 20B:
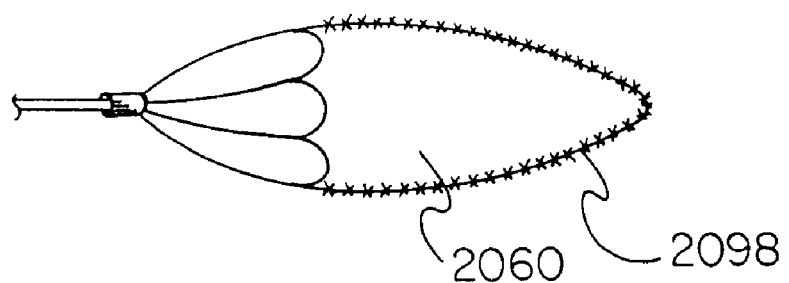
Figure 20C:
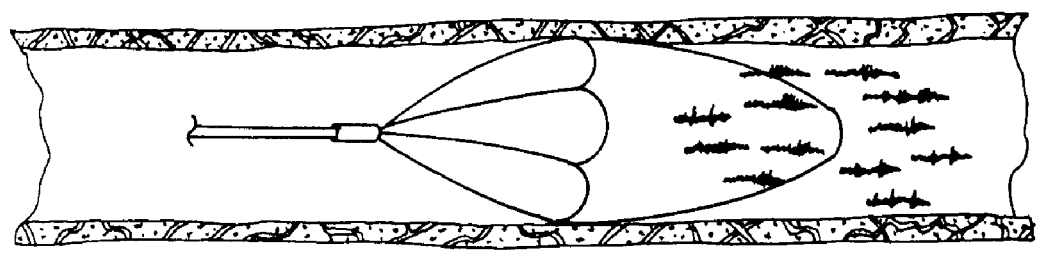

As shown in FIGS. 20A, 20B and 20C, a filter in accordance with the present invention can be used to deliver a pharmaceutical substance, anti-thrombotic agent, drug, etc., into the blood flow in a host lumen/vessel by deploying the filter in a lumen/vessel of interest. In FIG. 20A, a filter device such as that described in FIG. 17 above, can be loaded with a pharmacological agent in one or more different areas before delivery into the host. Thus, the drug can be loaded between layers of the filter media. The drug 2098 may be retained within the zone/space/area between the inner filter media 2060A and outer filter media 2060B ready to be delivered to the host.

Instead of using the filter-in-filter design of FIG. 17, any of the other filter configurations described herein can be used by imbibing the drug into the filter media itself. As shown in FIG. 20B, the drug 2098 can be imbibed into the media 2060 itself.

FIG. 20C illustrates drug administration in the host by deploying the drug delivering system of FIGS. 20A or 20B in a host lumen/vessel so that the blood flows through the filter media to elute the pharmacological agent, e.g., drugs. This method of localized drug delivery is effective for eluting a pharmacological agent contained either between adjacent layers of filter media or imbibed directly into the filter media. Fluid flow through the filter device of FIGS. 20A or 20B, or any other filter configuration described herein containing pharmacological agents provides a mechanism of mass transfer to downstream perfusion beds. The pharmacological agent could be pre-loaded into the filter or injected post deployment perhaps through an extension of the support/guidewire.

As shown in FIGS. 21A and 21B, occluding device 2175 can be formed as a detachable endoluminal filter frame that can be implanted in the host. The occluding device 2175 thus implanted can either be permanently implanted or retrieved at a later point in time, such as is required in vena cava filtering applications. As shown in FIG. 21A, blood flow through the host can be obstructed by the implantation of the filter frame apparatus 2100. The filter frame apparatus 2100, used as an indwelling or implantable occlusion device is shown in FIG. 21A. As shown in FIG. 21B, a guidewire or support wire 2180 includes a distal end 2181 that may be detached from proximal connector 2170 that is connected to the occluding device 2175 or filter frame apparatus 2100. The support wire 2180 is used to position or remove occluding device 2175 or filter frame apparatus 2100 from a lumen in a host. The guidewire tip 2181 may be of any design for detachment from or reattachment to proximal connector 2170. Thus, the guidewire 2180 can have any capture capability, including screw threads, magnetic, ball-and-socket, male-female attachment, bayonet, or any type of coupling that will allow the guidewire 2180 to detach or reattach to the proximal connector 2170 for placement or movement therein.

Figure 22A:
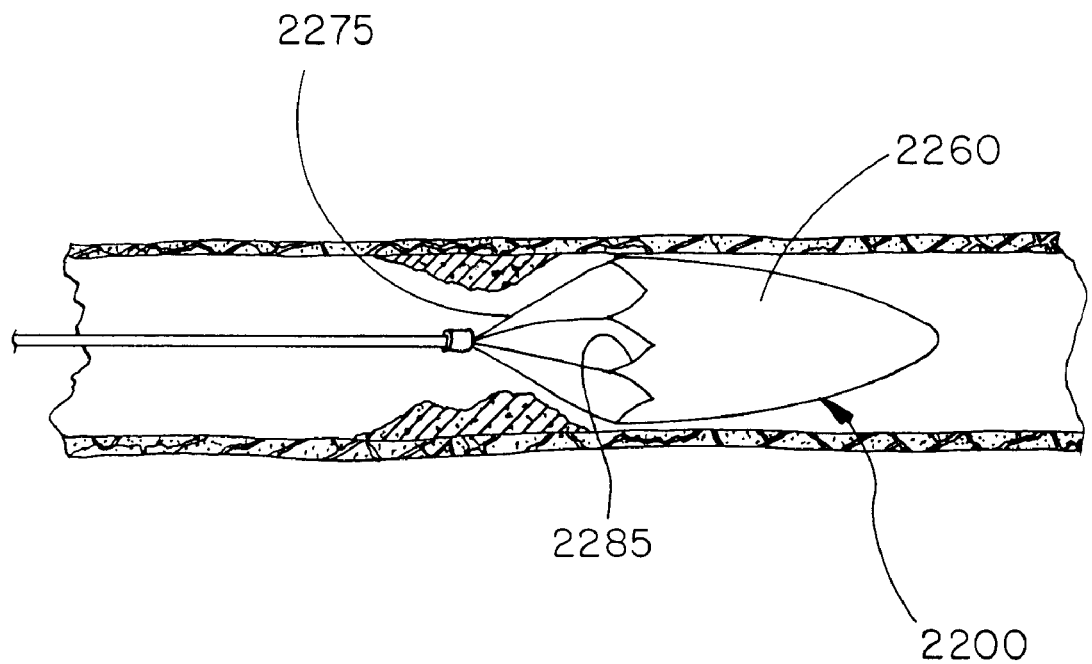
FIGS. 22A and 22B respectively illustrate the deployment of an obstruction remover and collection of removed lesion debris in a lumen/vessel of a host.
Figure 22B:
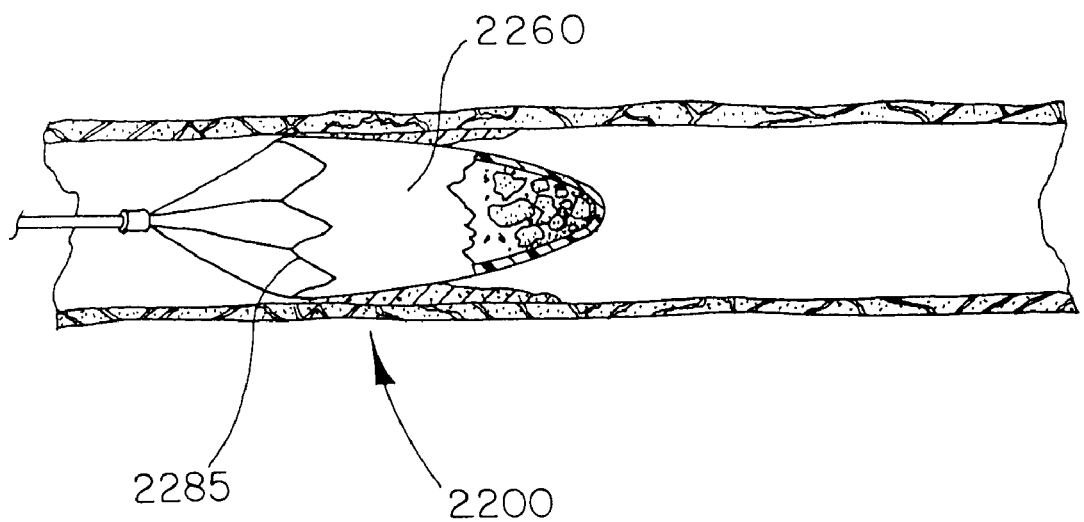

FIGS. 22A and 22B illustrate the use of a filter (similar to the filters 100 or 700, respectively shown in FIGS. 1D or 7C) to remove flow obstructions or to function as a thrombectomy device to remove intraluminal thrombus, for example. FIG. 22A shows an obstruction at the lumen wall in a blood vessel of the host. Though commonly the lesion will have formed in a restrictive manner, the lesion is shown in a cross-sectional area with an upper and a lower component, that has narrowed the effective diameter of the lumen. Filter 2200 includes sharpened support members 2285 to enable the filter to be used as a type of scraper. The frame 2275 shown herein includes a filter media 2260 as a "catch bag." In FIG. 22B, the filter 2200 is pulled with sharpened members 2285, effectively shearing the obstruction/lesion from the vessel wall of the host. As the lesion is sheared from the wall, sheared lesion parts are collected in the catch bag or filter media 2260. In this manner, the present filter frame can be used to remove lesions and collect the debris dislodged into the blood stream, to lessen the possibility of clotting downstream of the host vessel. This approach can likewise be used to capture and remove foreign objects from bodily passageways.

Figure 23A:
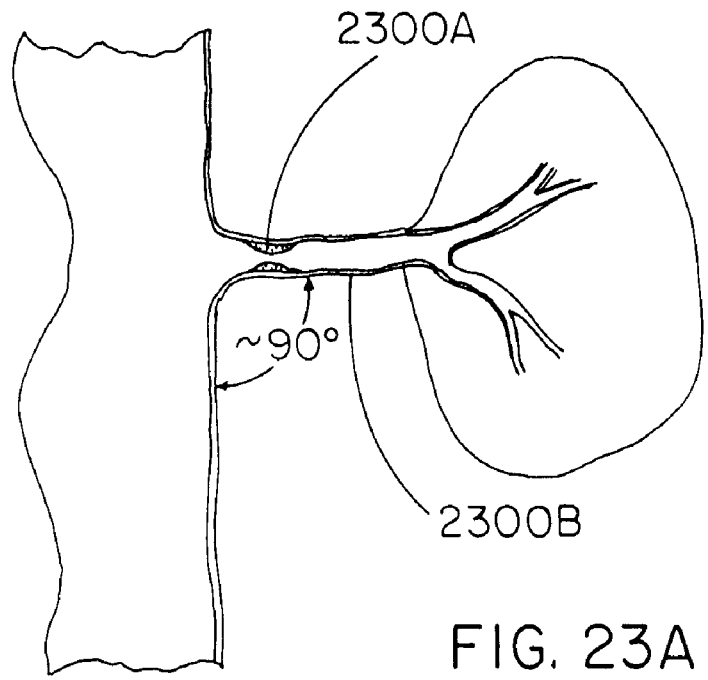
FIGS. 23A, 23B and 23C illustrate the use of an anchoring device for treatment of a lesion in tortuous vessels associated with renal anatomy.
Figure 23B:
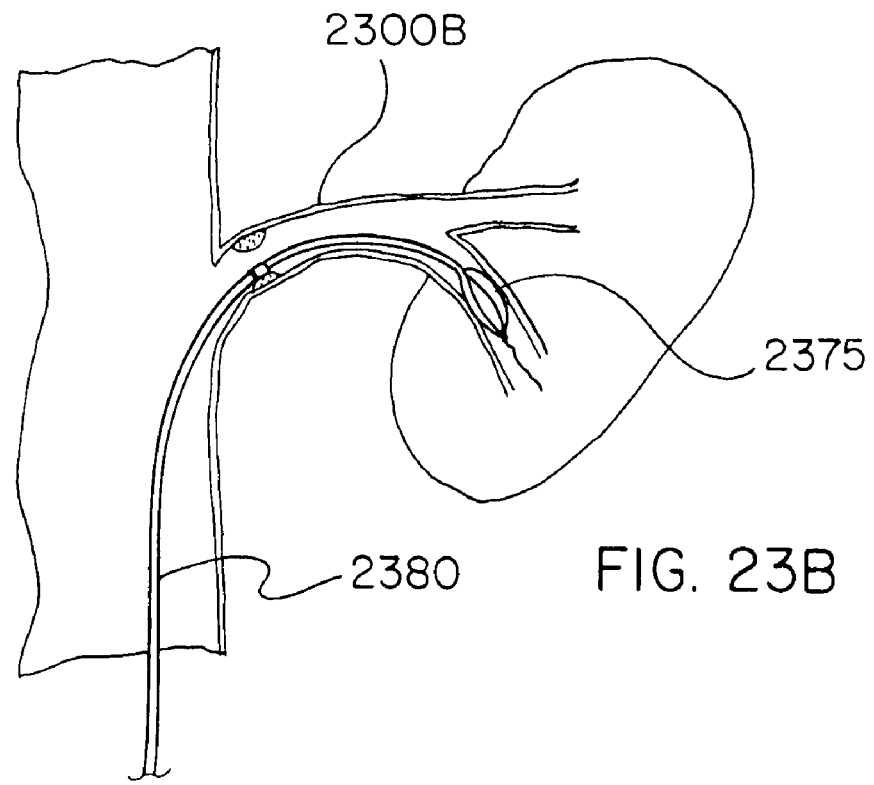
Figure 23C:
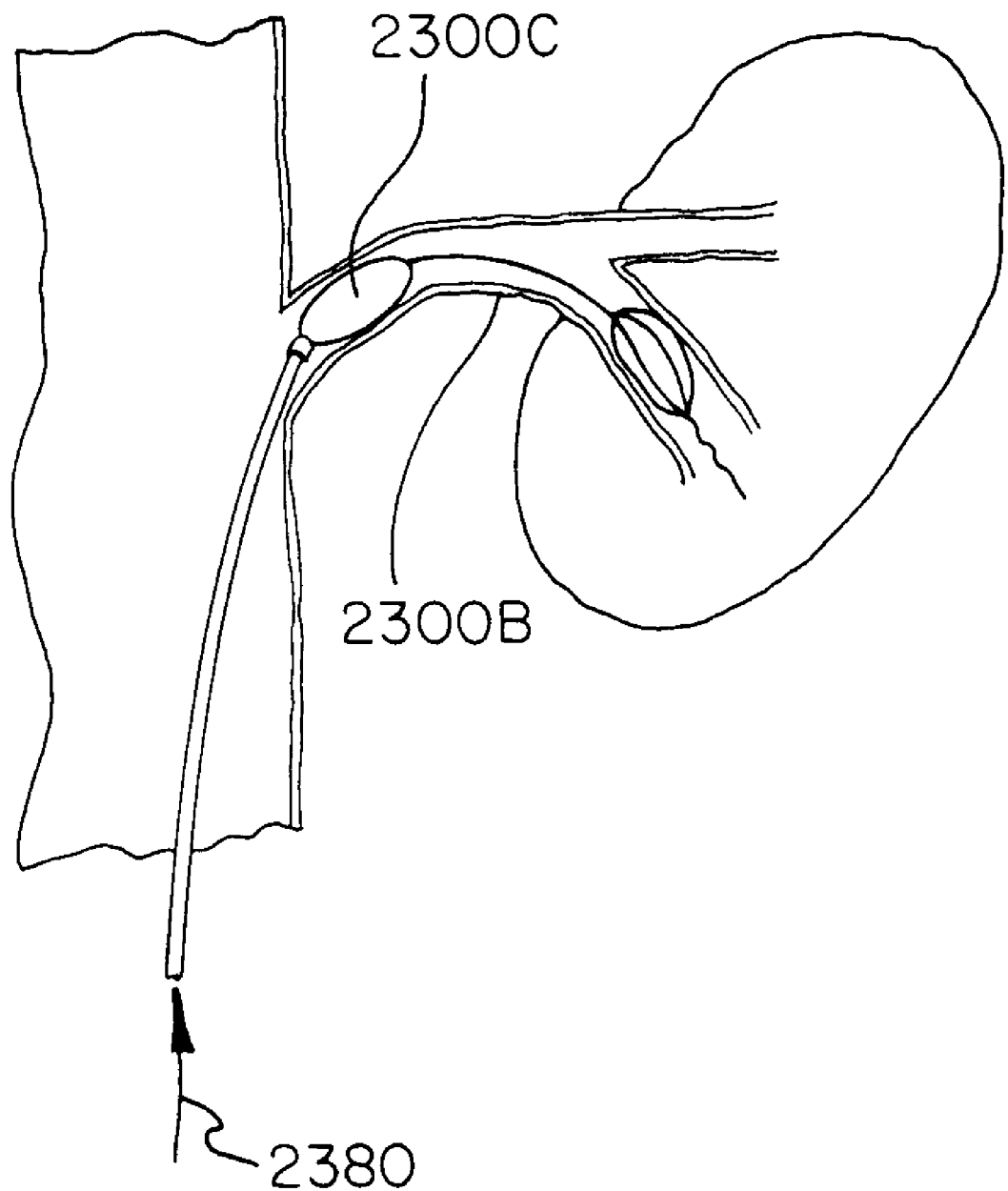

FIGS. 23A, 23B and 23C respectively illustrate the use of the inventive filter as an anchoring guidewire to facilitate the retention of a guidewire position in tortuous vessels of the renal circulatory system, and in particular for branch lumens offset at angles of approximately 90°. Using the inventive filter frame as an anchor avoids or minimizes damage to the host vessel, and specifically avoids or minimizes damage to the endothelium of the host lumen/vessel. FIG. 23A shows a lesion 2300A in a branch lumen/vessel 2300B associated with the renal anatomy of a host. In the non-limiting embodiment of FIGS. 23A-23C, the branch lumen 2300B includes an approximate 90° turn toward the existing anatomy shown. As illustrated in FIG. 23B a filter frame 2375 is positioned and anchored in a renal circulatory vessel 2300B to fix the position of the support wire 2380. A slight pressure is imposed on the support wire 2380 and the approximate 900 turn is extended to more than 90° without dislodging or altering the position of the guidewire in relation to the host anatomy as shown in FIG. 23B.

As shown in FIG. 23C, a therapeutic catheter 2300C can be inserted over the support wire 2380 of the filter frame to perform the intervention. As a result, therapy devices can more easily negotiate a greater than 90° bend as shown in FIGS. 23B and 23C. Such therapy devices include, but are not limited to balloons, stents, etc. A further useful aspect of this embodiment is that, during its use, a long "exchange length" guidewire is unnecessary. Since this device is capable of maintaining it's positioning after deployment, the necessity of "rapid exchange" or "monorail" catheters are obviated.

Figure 24A:
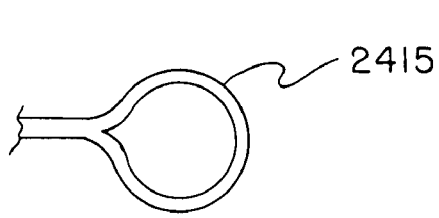
FIGS. 24A, 24B, 24C, 24D and 24E respectively illustrate a two dimensional frame, a three-dimensional resulting shape, an endovascular device formed from the three-dimensional frame and an open-ended windsock, the occlusion of a sacular aneurysm in a host lumen/vessel with the endovascular device and optional use of a stent lining the device.
Figure 24B:
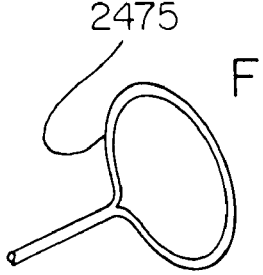
Figure 24C:
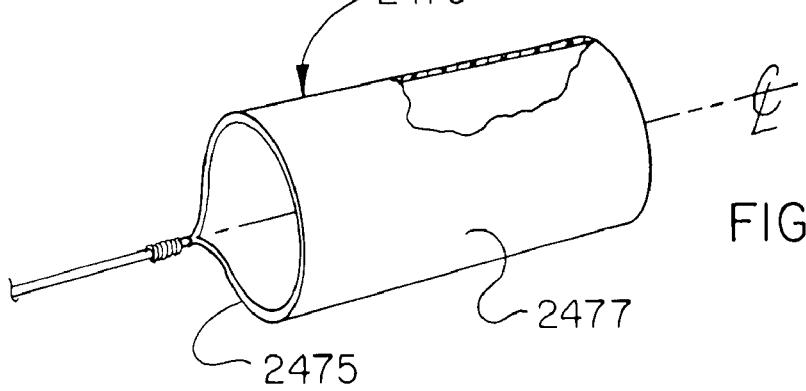
Figure 24D:
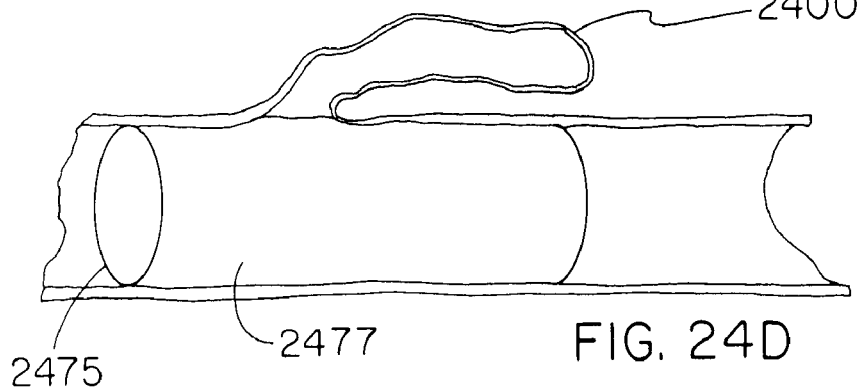
Figure 24E:
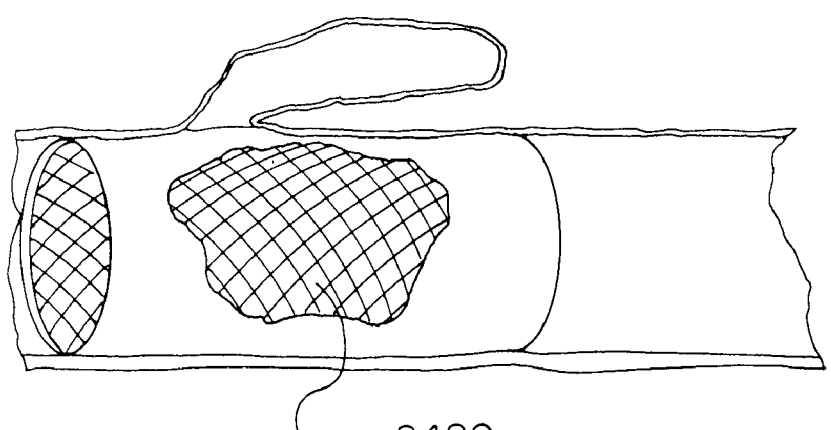

FIGS. 24A, 24B, 24C, 24D and 24E show a further embodiment of the present filter frame assembly, which is intended to function as an implantable endoprosthesis 2476. As shown in FIGS. 24A and 24B, the initial seamless filter frame 2475 is formed from a loop-type frame 2415 from the same precursor material. In FIG. 24C, the proximal end of an open-ended "windsock" shaped graft component 2477 is attached to the loop of the filter frame 2475 to form an endoprosthesis 2476. In FIG. 24D, the loop-type frame 2475 with the attached open-ended windsock is deployed proximal to an aneurysmal defect, and the windsock shaped graft component 2477 extends downstream of the frame, effectively excluding the aneurysm 2400A. Thus, frame and the opened ended sock function as an implantable prosthetic vascular conduit where the filter frame 2475 functions as an anchoring stent, and the open-ended sock functions as a biocompatible liner. This device, shown in FIG. 24E, may then be optionally lined with a stent 2480. This embodiment finds use as a stent and graft combination where the stent element would be deployed proximal to the intended therapy site and the graft element would be configured to be deployed by blood pressure.

Figure 25E:
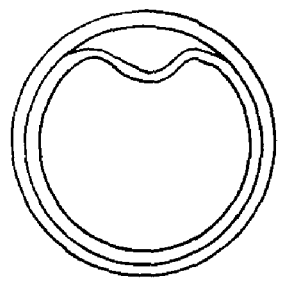

FIGS. 25A-25H illustrate an exemplary delivery system for deploying the present filter frame 2575 or filter 2500 of the present invention. FIG. 25A illustrates a frame 2575 or frame-filter 2500, such as frame 175 or frame-filter 100 of FIGS. 1D or 1E, frame 375 or frame-filter 300 of FIGS. 3B and 3C, or any of the other frame or frame-filter assembly herein described, attached to a support or guidewire 2580 and positioned within a tubular delivery sheath 2500A of a delivery catheter. FIGS. 25B-25D illustrates front views taken from sectional plane A-A of FIG. 25A, but without the frame 2575 or frame-filter 2500. The section A-A1 (FIG. 25B) illustrates a dual lumen extrusion catheter sheath. Section A-A2 (FIG. 25C) illustrates a single lumen extrusion having an additional covering formed from a shrink tube. Section A-A3 (FIG. 25D) illustrates a second lumen adhered to the inner diameter of the tubular delivery sheath 2500A of FIG. 25A.

Figure 25F:
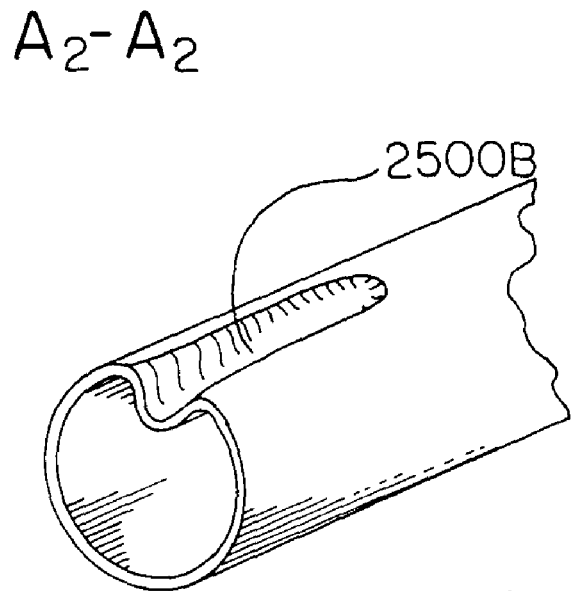
FIGS. 25F, 25G and 25H respectively illustrate three-dimensional top views of catheter tube having a channel indented in its surface adjacent its distal end, a sleeve covering the indented channel and a guidewire located in the sleeve covered-indented channel.
Figure 25G:
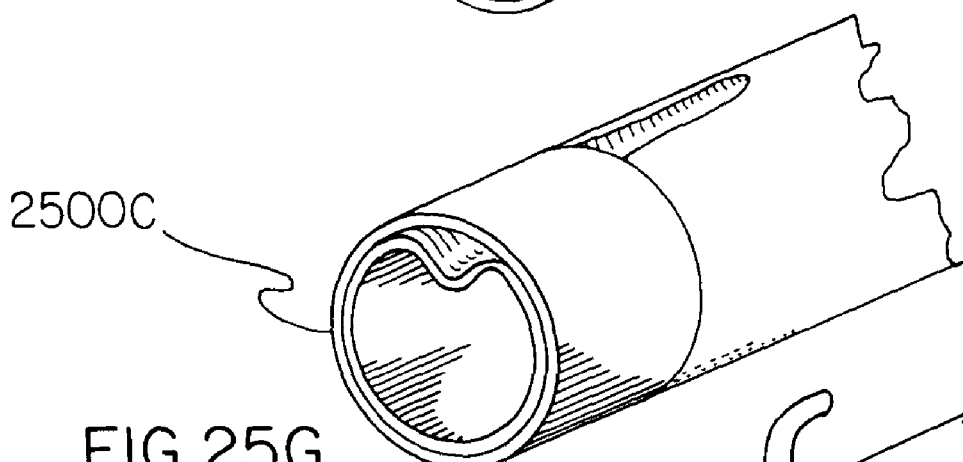
Figure 25H:
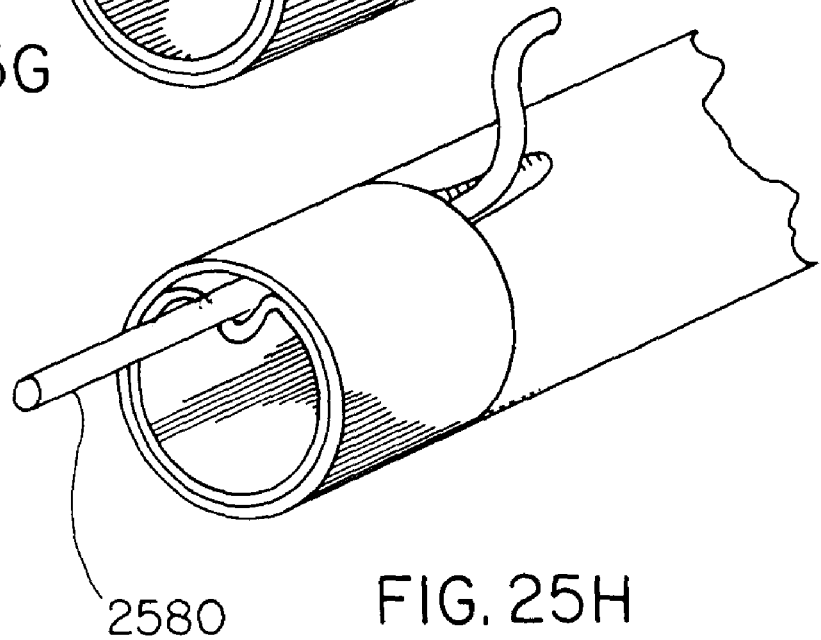

FIG. 25E-25H illustrate the perspective detail of external guidewire 2580 loading of a catheter lumen. FIG. 25E is a front view of the FIG. 25G. FIG. 25F illustrates the catheter having a longitudinally extending indented channel, which, as seen in FIG. 25G is circumscribed by a tubular section 2500C. The guidewire 2580 is inserted into the longitudinally extending channel 2500B between the external wall of the catheter and the tubular section 2500C. In use, a filter frame or filter-frame construct is pre-loaded into the distal end of the sheath adjacent to an exterior wire guide channel. The exterior wire guide is adapted to receive a guidewire in a rapid exchange configuration, however, unlike the prior art, the filter frame and guidewire 2580 are completely segregated and no aperture exists.

Figure 26A:
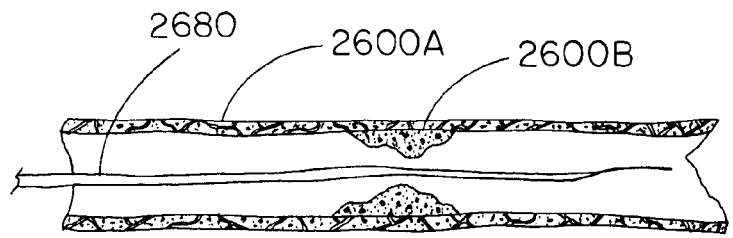
FIGS. 26A, 26B, 26C 26D and 26E respectively illustrate steps followed in treating a lesion in a host lumen/vessel.
Figure 26B:
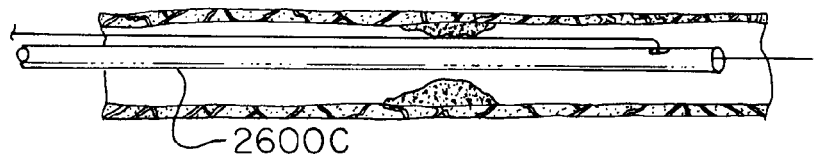
Figure 26C:
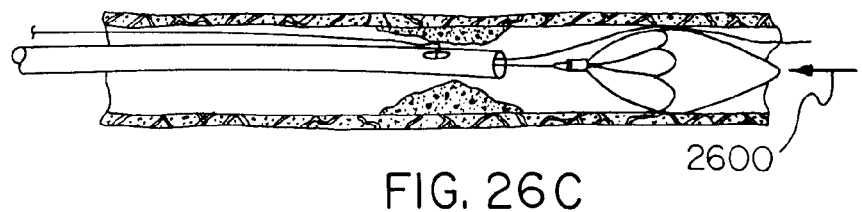
Figure 26D:
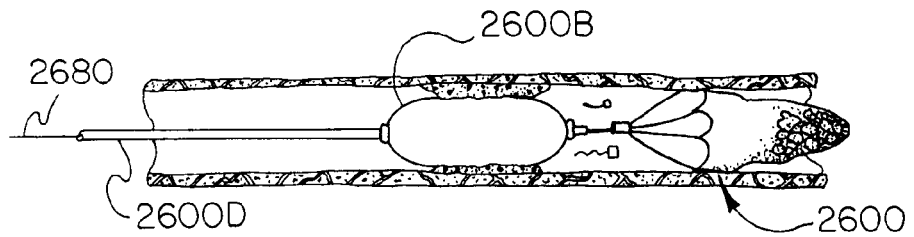
Figure 26E:
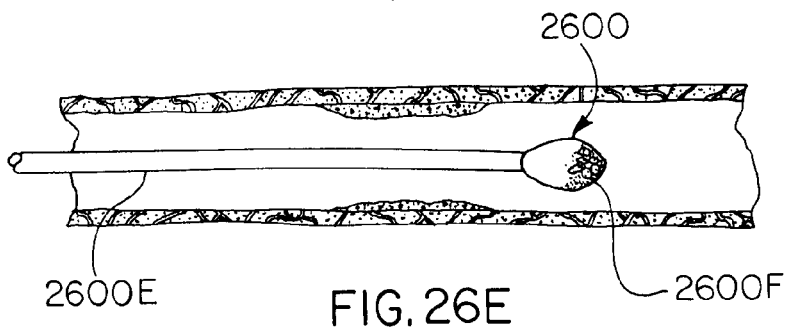

FIGS. 26A, 26B, 26C, 26D and 26E illustrate a method of using a filter frame assembly 2600 in accordance with the present invention. In FIG. 26A, a lumen/vessel 2600A of the host has a lesion 2600B. A guidewire 2680 is deployed into the lumen/vessel 2600A past the target lesion 2600B. Thereafter, guidewire 2680 is back-loaded into the delivery system 2600C, such as the one described in FIGS. 25B-25D, 25F-25G, or FIG. 27B. Then the delivery sheath 2600C is advanced across the target lesion 2600B. The delivery sheath 2600C is withdrawn, thereby allowing a self-expanding filter 2600 to deploy. The self-expanding filter 2600 is normally designed to deploy spontaneously after the delivery sheath 2600C has been withdrawn in this manner. Thus, as shown in FIG. 26C, the filter 2600 is deployed downstream of the lesion 2600B. A therapeutic catheter 2600D, such as an angioplasty balloon, is routed over the support wire 2680 in FIG. 26D to treat target lesion 2600B. As also shown in FIG. 26D, when the therapy is performed, the filter 2600 functions to capture any emboli dislodged or removed by the therapeutic catheter 2600D. Thereafter, as illustrated in FIG. 26E, the filter 2600 is removed via insertion of a tubular capturing catheter 2600E over the support wire and retraction of the filter 2600 into the capture catheter 2600E is performed. This retraction can be performed by pulling the filter 2600 partially back into the capture catheter lumen 2600E, effectively trapping the emboli 2600F. In this manner, the lesion is dissipated through a therapeutic catheter without the result of any of the dislodged emboli or debris dislodging into the host.

Figure 27A:
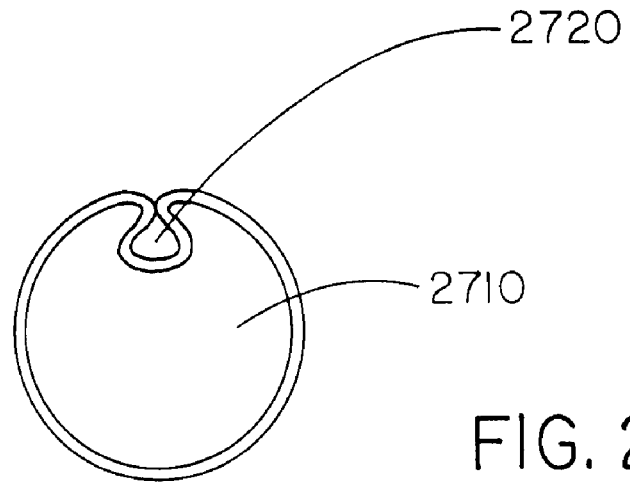
FIGS. 27A, 27B and 27C respectively illustrate a view of the distal tip a delivery catheter with an alternate auxiliary lumen configuration, a three-dimensional top view of the auxiliary lumen configuration and an auxiliary lumen mounted guidewire.
Figure 27B:
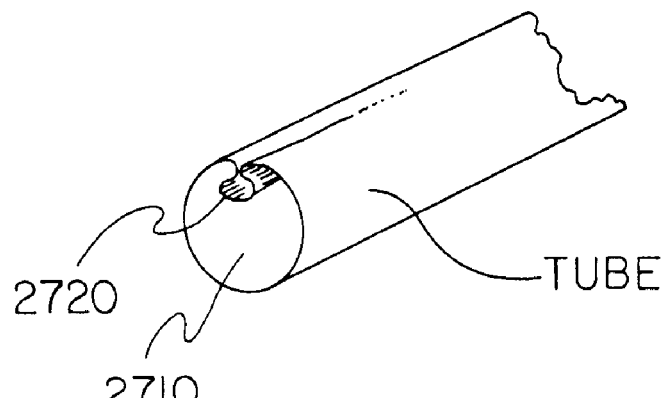
Figure 27C:
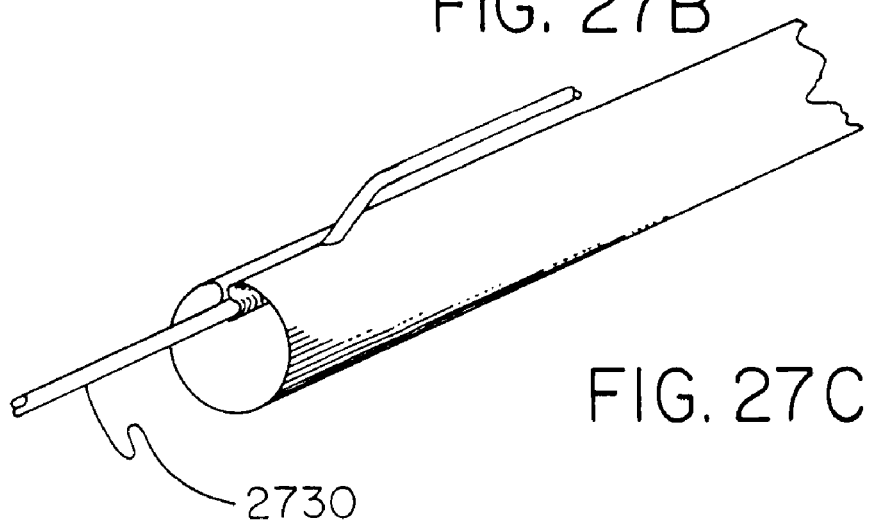

FIGS. 27A, 27B and 27C illustrate a lumen 2710 having an auxiliary, internally positioned channel 2720 for receiving a guidewire 2730. FIG. 27A illustrates the tip of the sheath having an internally located, peripherally positioned auxiliary channel 2720 formed by "pinching" the end of the tube wall as shown in FIG. 27B. FIG. 27C shows the guidewire 2730 inserted through into the slit opening in the side of the catheter and exiting the tip.

Figure 28:
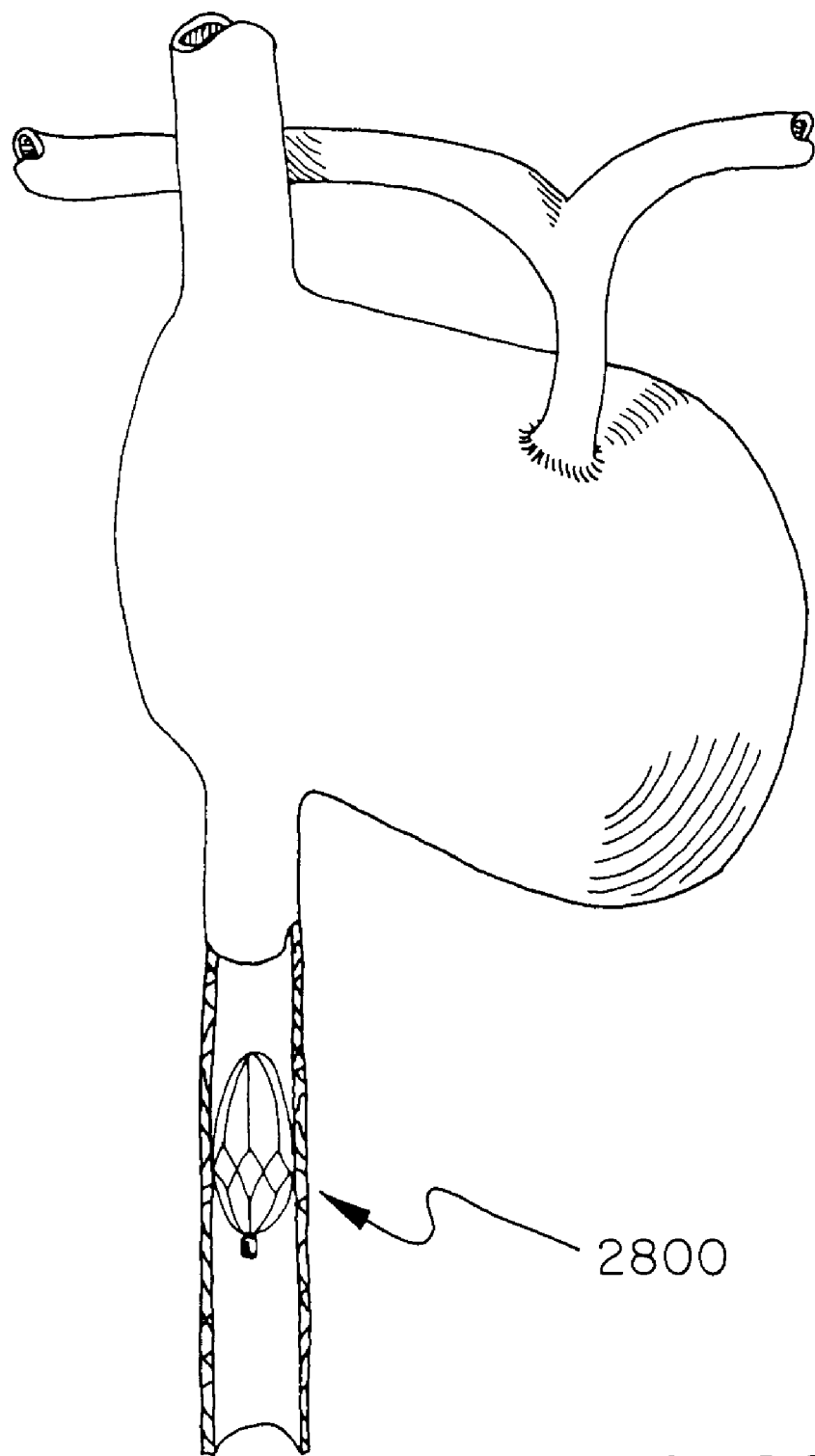
FIG. 28 illustrates a configuration of the present invention deployed as an implantable vena cava filter.

FIG. 28 illustrates the use of the inventive filter 2800, as a vena cava filter. Since the inventive filters described herein may be readily detachable, the filter 2800 can be readily detached from a deployment guidewire.

Figure 29A:
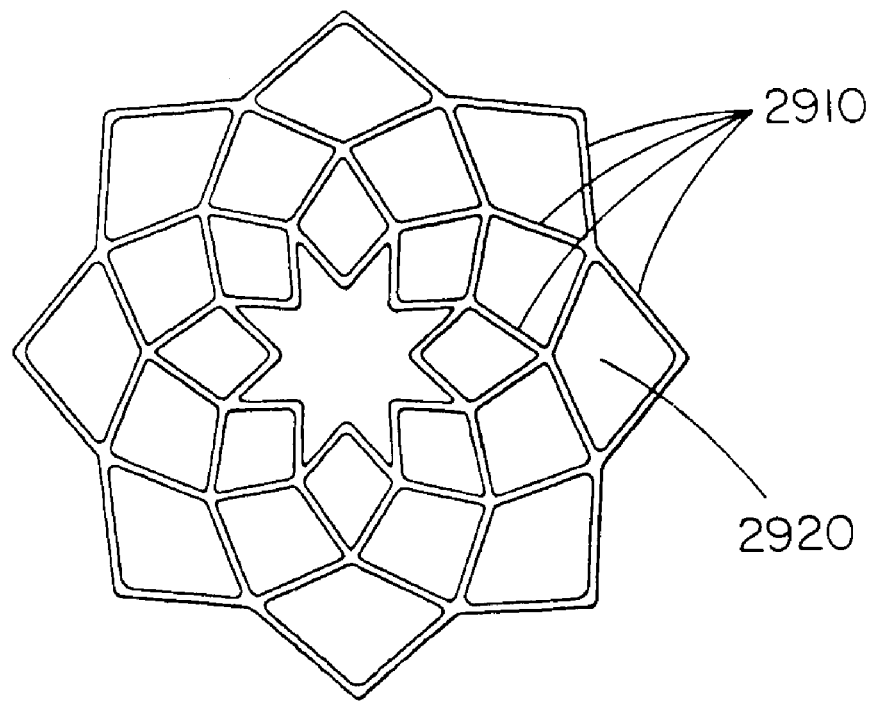
FIGS. 29A and 29B respectively illustrate an alternate two-dimensional planar configuration of the present invention, and a three-quarter isometric view of this configuration formed into a three-dimensional shape designed for use as an implantable stent.
Figure 29B:
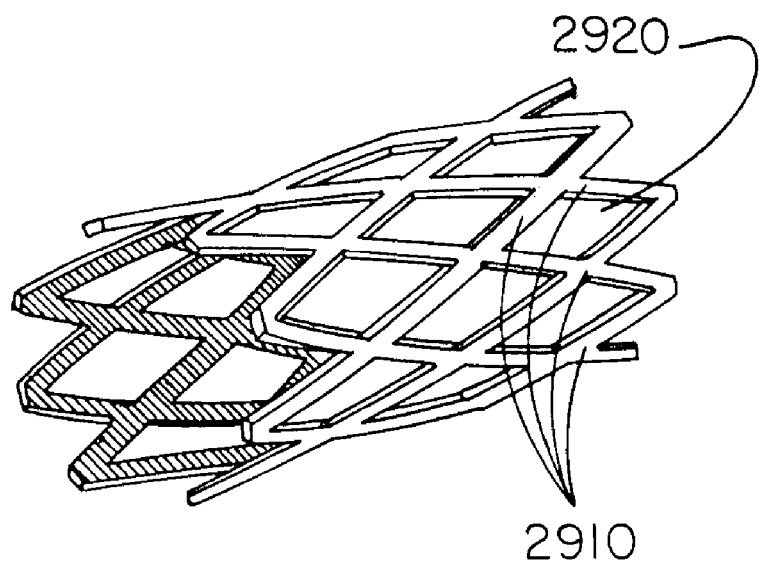

FIG. 29A illustrates a planar two-dimensional seamless pattern, formed from metallic material, or any other suitable biocompatible material. FIG. 29B illustrates a three-dimensional stent member formed from the planar two-dimensional pattern of FIG. 29A, for use as an intraluminal stent. When extremely thin wall sections are required, such as in coronary stents, it is appropriate to fabricate the device from a planar sheet of material. Planar material can be manufactured thinner than tubing due to the extra requirements of concentricity placed upon tubing stock. It should be noted that although only one design has been depicted, a wide variety of patterns and cell geometries may be produced from planar material. The various cell geometries are defined by the interconnected struts of the stent. In FIGS. 29A and 29B four interconnected struts 2910 define the four sided cell 2920. This planar material may be metallic or polymeric or a combination thereof, and in any case, may also be porous. Once the flat pattern is fabricated, it is formed into a 3-D shape (in the depicted instance, an open mesh tube). The formed stent may be either plastically deformable (and thus made from a malleable starting material) or may be self-expanding, in which case a superelastic, pseudo-elastic or shape memory material may be used. Subsequent processing such as thermal treatment, diametric reduction, de-burring and polishing may be incurred, depending upon the specific stent design. It should be understood that multiple 3-D stent "units" could be manufactured in such a way and attached together to form a much longer device.

Figure 30:
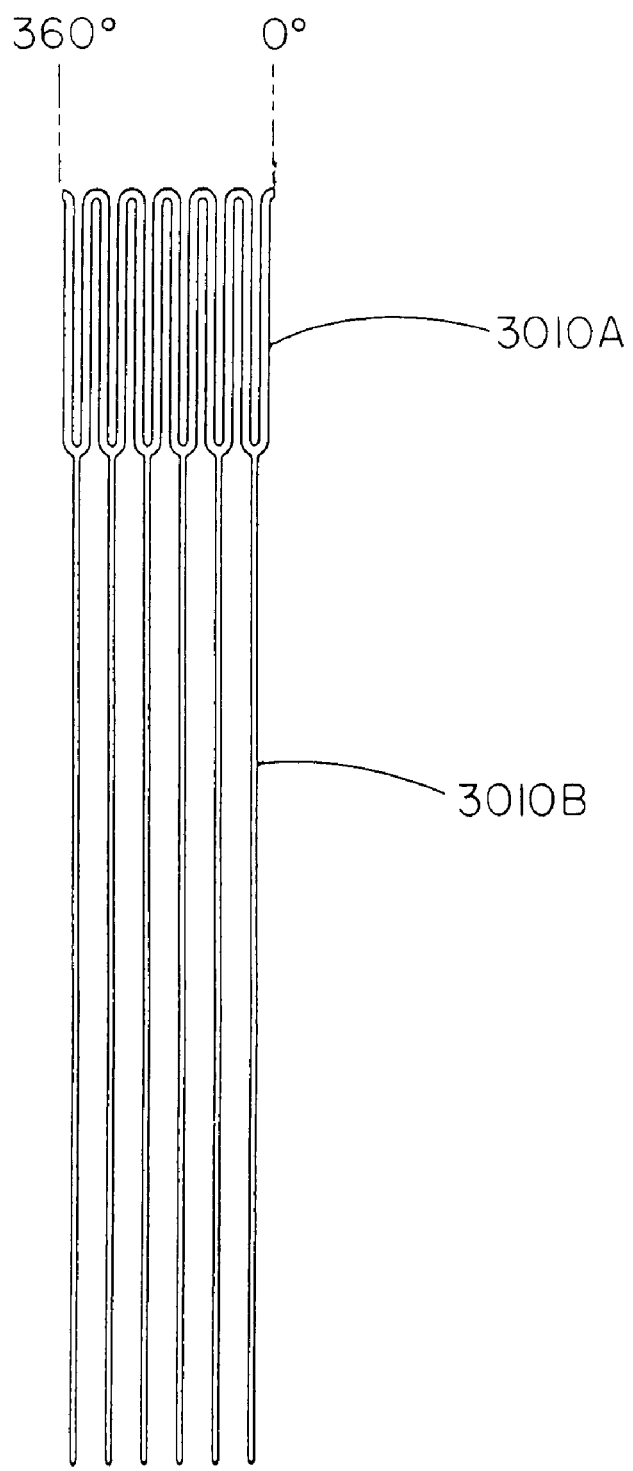
FIG. 30 is a flat pattern view of a filter frame and integral tether elements as would be cut from a tube.

FIG. 30 depicts a view of a flat pattern of filter frame 3010A and integral tether element 3010B geometry as it would be cut from a tube. This tube may be made of a shape memory alloy such as Nitinol. Cutting could be accomplished by a variety of methods including machining, laser cutting, stamping or etching.

Figure 31:
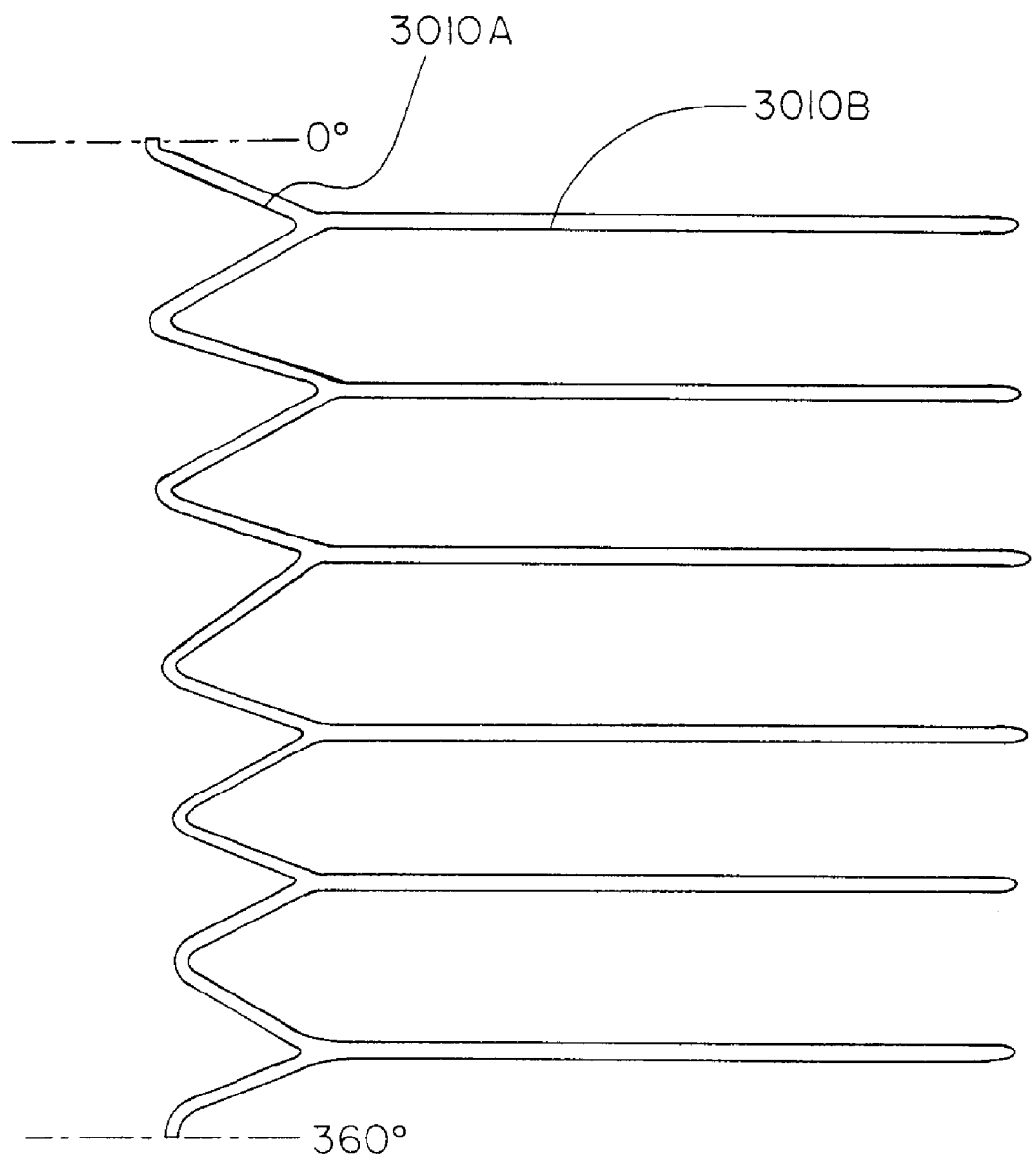
FIG. 31 is a flat pattern view of a filter frame and integral tether elements after being formed and annealed at a functional size.

FIG. 31 depicts the flat pattern geometry of FIG. 30 subsequent to forming and annealing at a larger, functional size. Upon annealing, the filter frame 3010A resiliently maintains this larger diametrical profile and the at least one tether element 3010B extends seamlessly from it.

Figure 32A:
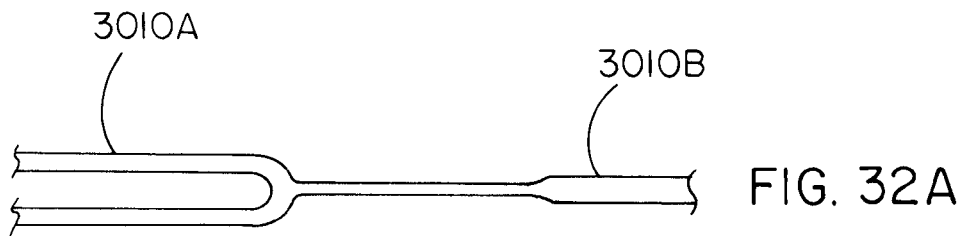
FIGS. 32A, 32B, 32C, 32D and 32E respectively show variations in the tether geometry, designed to allow the tethers to articulate with respect to one another and to the filter frame itself.
Figure 32B:
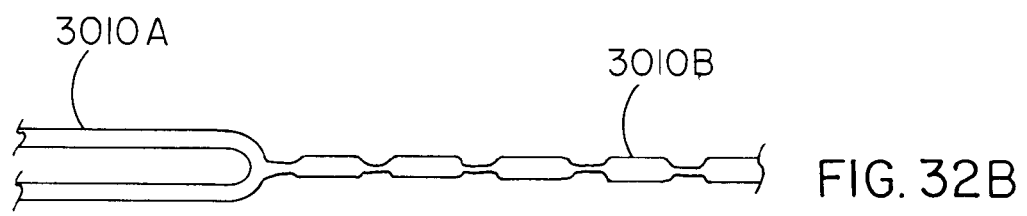
Figure 32C:
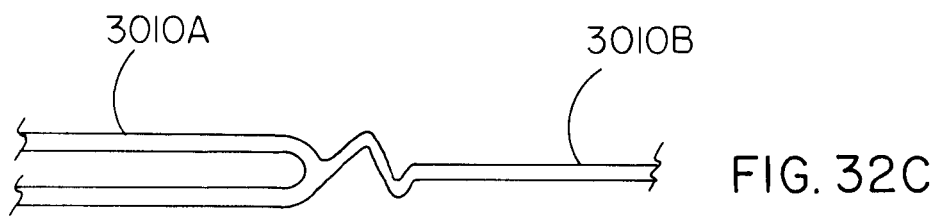
Figure 32D:
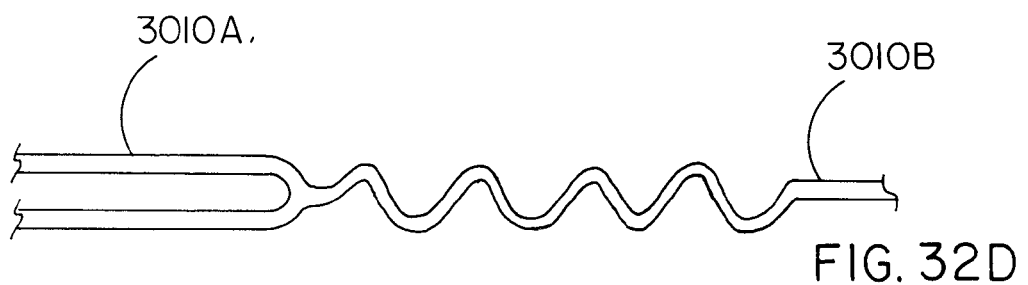
Figure 32E:
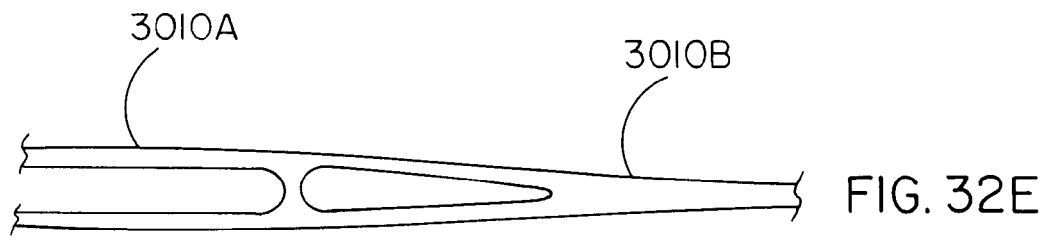

FIGS. 32A-32E depict alternate articulation segments formed as an integral part of the tether element thereby forming different tether element geometries, which allow articulation of the tether elements 3010B in relation to the filter frame 3010A. FIG. 32A depicts the tether element 3010B with an area of reduced strut width e.g. reduced cross-sectional area, to allow increased flexibility. FIG. 32B depicts tether element 3010B with several individual areas of reduced strut width to allow increased flexibility. FIG. 32C depicts tether element 3010B with a reduced width and formed "hinging" area to increase flexibility. FIG. 32D depicts tether element 3010B with a reduced width and several formed "hinging" areas to increase flexibility. FIG. 32E depicts tether element 3010B divided in two for a portion of its length. This division effectively increases the tether element flexibility so as to allow articulation. The articulation segment of the tether element, therefore, is configured to enhance the flexibility of the filter apparatus (and thus, conformance to the host vessel wall) as well as to minimize inadvertent trauma translated to the host vessel wall by movement or manipulation of the guidewire.

An articulation segment of the tether elements or struts is a desirable feature in that it allows adequate vessel wall apposition of the filter frame when the filter device is deployed in a curved segment of anatomy. In a curved segment, the tether element articulates and deflects to adjust for a non-linear deployment situation (See FIG. 14). Thus, the filter frame itself can maintain an uncompromised and fully deployed condition. Likewise, because of its ability to attenuate longitudinal translation, the articulation segment provides a means of mitigating trauma of the host vessel wall due to guidewire manipulation. It should also be noted that the required deflection and articulation of the tether elements could be bought about by metallurgical means rather than, or in combination with, geometrical means. For instance, the tether 3010B and frame 3010A elements of FIGS. 32A-E, although seamless and integral, may be exposed to different thermal processing parameters (for example: through the use of fixturing to provide differential heat sink qualities), thus rendering the tether 3010B ductile and pliable while the frame 3010A maintains the stiffness required for adequate vessel wall apposition.

The articulation segments, though described with respect to the various frame patterns can be incorporated into any of the endovascular devices described herein. An articulation segment is a localized region that provides enhanced longitudinal flexibility. A localized region may have a cross-sectional area that is the same as the remaining part a strut, but differs in geometry. Alternatively, the localized region could have the same geometry but a different cross-sectional area, or both the cross-sectional area and geometry of the localized region differ from the remaining part of the strut. An endovascular stent can have articulation segments in any of the interconnected struts of FIGS. 29A and 29B.

EXAMPLES OF THE PRESENT INVENTION

Example 1

Nitinol Sheet Filter Frame and Integral Tethers

A radially-symmetric geometrical pattern comprising interconnected struts forming closed polygonal shaped cells was chemically etched from a sheet of Nitinol (NiTi) to produce a skeletal filter frame. The etching, preferably photo-etching of Nitinol (Kemac Technologies, Irwindale, Calif.) is continued to achieve a desirable material thickness, to optimize the moment of inertia of the struts and to polish the surface finish.

This filter frame is then subjected to a thermal treatment to set the phase transition temperature of the NiTi to approximately 37° C. by heating the filter frame to a temperature of about 450° C. for about 10 minutes in an air convection oven (Carbolite Corporation, Sheffield, England ) followed by a rapid quench in ambient temperature water.

The NiTi filter frame was then laminated between two (2) layers of an adhesive-coated porous polymer. The layers were positioned with the adhesive sides facing toward each other, and facing toward the NiTi. The adhesive was used to adhere the layers of film together as well as to the NiTi wire framework. A sacrificial porous polymer cushion material was used on each side of the device during this lamination procedure to provide compliance of the surface during compression. This compliance allows the earlier mentioned porous polymer membrane to conform to the wire shape. The composite subassembly which included cushion, porous polymer/adhesive laminate, NiTi, adhesive/porous polymer laminate, and cushion layers was then compressed in a SST fixture and heat treated at 320° C. for 45 minutes in an air convection oven (Grieve Oven, The Grieve Corporation, Round Lake, Ill.).

Once the 'sandwiched' device was removed from the heat source and allowed to cool, the sacrificial cushion material was peeled away from each side of the device and the NiTi wires were disengaged from the fixture. A circular shape of approximately 0.625" in diameter was trimmed into the porous polymer using a 20-watt carbon dioxide laser. The remainder of porous polymer was trimmed from the wire frame by hand and discarded.

Following the laser trimming operation (which can also be used to create the necessary pores in the filter media), the radially-oriented arms (struts) of the device were folded up and back on themselves to achieve a hollow, three dimensional, semi-conical shape. To maintain the device in this configuration, the NiTi struts were inserted into a SST tube. This tube measured approximately 0.05" in length×0.035" outer diameter×0.025" inner diameter. This tube and indwelling NiTi wires were then crimped to a 0.014" diameter guidewire to provide a guidewire based endoluminal embolic protection device. The device resembled a three dimensional "whisk" shape with a pleated porous polymer filter element attached to it.

The resulting pleats are designed to increase filter media surface area over the generally conical shapes found in the prior art. This increase in surface area also allows for a shorter filter length which enhances deliverability of the device by a) decreasing friction in the delivery catheter and b) improving device overall flexibility.

Example 2

Nitinol Tube Filter Frame and Integral Tethers

A 1.3 mm Nitinol tube with a wall thickness of approx 0.1 mm (obtained from Nitinol Devices and Components, Fremenot, Calif.) was laser cut (Laserage Technologies Inc, Waukegan, Ill.) to a single, undulating 6 apex ring geometry with integral tethers. This frame was then lightly grit blasted at 40 psi with 20 micron silicon carbide media in a grit blasting machine made by Comco Inc, Burbank, Calif. The ring with integral tethers was then gently pushed up a tapered mandrel until it achieved a functional size of approx. 6 mm. The ring, tethers and mandrel were then subjected to a thermal treatment to set the phase transition temperature of the NiTi to approximately 37° C. in an air convection oven (Carbolite Corporation, Sheffield, England ) One skilled in the art will realize that variances in the geometry, metallurgy, thickness and heat treating of the filter frame can all be varied to create alternate embodiments with varying desirable properties. The ring and tethers (now at functional size) were then lightly coated with an fluorinated ethylene propylene (FEP) powder (FEP 5101, available from Dupont Corp, Wilmington, Del.) by first stirring the powder in a kitchen blender (Hamilton Beach Blendmaster, Wal-Mart) after the power was mixed into a "cloud", the frame was hung into the blender for enough time for FEP to build up onto the surface of the ring. The frame, now coated with FEP powder was hung in an air convection oven (Grieve Oven, The Grieve Corporation, Round Lake, Ill.) set at 320° C. for approx. one minute followed by air cooling to room temp.

The NiTi frame was then set atop a filter sack and attached though the application of localized heat (the heat causing the FEP coating on the ring to re-melt and flow onto the surface of the filter sack, thus providing a biocompatible thermoplastic adhesive). The tether lines were then routed through a gold tube (Johnson Matthey, San Diego, Calif.) radiopaque marker. The tethers were pulled until they began to apply tension to the frame. A guidewire was then inserted into the gold band (from the opposite direction of the tether lines). The marker band was then crimped to secure the tethers and guidewire together. A small amount of instant adhesive (Loctite 401, Loctite Corp, Rocky Hill, Conn.) was applied to create a smooth transition from the guidewire to the OD of the gold band. One skilled in the art will realize that attachment of the filter to the guidewire could be accomplished by adhesion, welding, soldering, brazing, a combination of these, or a number of other methods.

Upon drying, this embodiment of the endoluminal embolic filter is ready for testing.

Various illustrative examples of the invention have been described in detail. In addition, however, many modifications and changes can be made to these examples without departing from the nature and spirit of the invention.

What is claimed is:

1. An endovascular device, comprising:
a uni-body frame having a proximal end, a distal end and a longitudinal axis extending therebetween, said uni-body frame having at least two support members, at least two struts and at least two articulated segments, said uni-body frame circumscribing said axis and located at about the distal end;
wherein the at least two support members includes a first support member and at least one secondary support member, wherein the at least one secondary support member is spaced distally from and attached to said first support member, wherein one of the at least one secondary member defines the distal end of the uni-body frame;
wherein the at least two struts extend from the first support member towards said proximal end; and
wherein the at least two articulated segments are located to extend longitudinally between the first support member and the at least one secondary support member; and
a one piece filter media configured to collect embolic material is attached to the first support member, wherein the one piece filter media circumferentially covers said at least two support members circumscribing said axis; and
the distal end of the filter media is circumferentially disposed about a guidewire wherein the circumferentially disposed filter media further comprises at least one point of contact between the filter media and the guidewire, and a majority of the filter media extends beyond the distal end of the uni-body frame.

2. The device of claim 1, wherein at least one of the at least two support members includes at least one radiopaque marker.

3. The device of claim 1, wherein at least one of the at least two struts includes at least one radiopaque marker.

4. The device according to claim 1, wherein the one piece filter media includes a pharmacological agent.

5. The device according to claim 4, wherein said pharmacological agent is selected from the group consisting of anti-thrombotic agent, drug, and combinations thereof.

6. The device according to claim 1, wherein the one piece filter media comprises at least two layers.

7. The device according to claim 6, further comprising a pharmaceutical substance.

8. The device according to claim 1, further comprising an articulation segment on at least one of said at least two struts.

9. The device according to claim 1, wherein the filter media has a substantially windsock configuration.

10. The device according to claim 1, wherein the filter media has a substantially tapered configuration.

11. The device according to claim 1, wherein the struts are configured to be more flexible than the support members.

12. The device according to claim 11, wherein the struts have a different cross-sectional area than the support members.

13. The device of claim 1 wherein the filter media comprises expanded polytetrafluoroethylene.

14. A device, comprising:
a uni-body frame having a proximal end, a distal end and a longitudinal axis extending therebetween, said uni-body frame having at least two support members, a first set of struts, and at least two articulated segments, said uni-body frame circumscribing said axis;

wherein the at least two support members includes a first support member and at least one secondary support member, wherein the at least one secondary support member is spaced distally from and attached to said first support member, wherein one of the at least one secondary member defines the distal end of the uni-body frame, wherein the at least two support members are capable of expanding to a substantially similar outside diameter in order to provide a seal region against a vessel wall;

wherein the first set of struts extends from the first support member towards said proximal end; and wherein the at least two articulated segments are located to extend longitudinally between the first support member and the at least one secondary support member; and a filter media including a pharmaceutical substance, wherein the filter media is circumferentially attached to one of the at least two support members, wherein said filter media circumscribes said axis and is configured to collect embolic material, and wherein the distal end of the filter media extends distally beyond the uni-body frame and is circumferentially disposed about a guidewire, wherein the circumferentially disposed filter media further comprises at least one point of contact between the filter media and the guidewire.

15. The device according to claim 4, further comprising a radio-opaque marker arranged between the at least two support members.

16. The device according to claim 14, further comprising radiopaque markers arranged on the uni-body frame.

17. The device according to claim 14, wherein the filter media comprises at least two layers.

18. The device according to claim 17, wherein a pharmaceutical substance is loaded between the two layers.

19. The device according to claim 14, wherein the filter media has a substantially parabolic configuration.

* * * * *